US007205450B2

(12) United States Patent
Cook et al.

(10) Patent No.: US 7,205,450 B2
(45) Date of Patent: Apr. 17, 2007

(54) DMI1 GENE ENCODES A PROTEIN THAT IS REQUIRED FOR THE EARLY STEPS OF BACTERIAL AND FUNGAL SYMBIOSES

(75) Inventors: Douglas R. Cook, Davis, CA (US); Ramachandra V. Penmetsa, Sacramento, CA (US); Gyorgy B. Kiss, Szeged (HU); Jean-Michel Ane, Davis, CA (US); Jean Denarie, Castanet-Tolosan (FR)

(73) Assignees: The Regents of the University of California, Oakland, CA (US); Institut National de la Recherche Argronomique (INR), Paris (FR)

( * ) Notice: Subject to any disclaimer, the term of this patent is extended or adjusted under 35 U.S.C. 154(b) by 389 days.

(21) Appl. No.: 10/739,736

(22) Filed: Dec. 17, 2003

(65) Prior Publication Data

US 2005/0081262 A1   Apr. 14, 2005

Related U.S. Application Data

(60) Provisional application No. 60/510,098, filed on Oct. 8, 2003.

(51) Int. Cl.
  C12N 15/09   (2006.01)
  C12N 15/82   (2006.01)
  C12N 15/29   (2006.01)
  A01H 5/00    (2006.01)
  A01H 5/10    (2006.01)

(52) U.S. Cl. .................. 800/278; 536/23.6; 435/320.1; 435/468; 800/298; 800/295

(58) Field of Classification Search ................. 800/278, 800/298, 295; 435/468, 320.1
See application file for complete search history.

(56) References Cited

FOREIGN PATENT DOCUMENTS

WO   WO 02/102841   12/2002

OTHER PUBLICATIONS

Ané, Jean-Michel et al. (2004) "Medicago Truncatula DMI1 Required for Bacterial and Fungal Symbioses in Legumes" *Science*, 303:1364-1367.
Cook, Douglas R. et al. (2003). "Towards the Complete Gene Inventory Function of the Medicago Truncatula Genome." Annual Report National Science Foundation, Award# 0110206, University of California, Davis, (Jun. 2003) pp. 1-66.
Ane, Jean-Michael, et al. Medicago Truncatula DMI1 Required for Bacterial and Fungal Symbioses in Legumes, Science, 303:1364-1367 (Feb. 27, 2004).
Amor, Besma Ben et al. (2003) "The *NFP* locus of *Medicago truncatula* controls an early step of Nod factor signal transduction upstream of a rapid calcium flux and root hair deformation" *The Plant Journal* 34: 495-506.
Anantharaman, Vivek et al. (2001) "Regulatory Potential, Phyletic Distribution and Evolution of Ancient, Intracellular Small-molecule-binding Domains" *J. Mol. Biol.* 307: 1271-1292.
Ané, Jean-Michel et al. (Oct. 2003) "Progress towards the cloning Medicago truncatula DMI1, a gene that is required for early steps in bacterial and fungal symbiosis" *Western Section of the American Society of Plant Biologists meeting on Plant Genomics 2003*; UC Davis: 11 pages.
Ané, Jean-Michel et al. (2002) "Genetic and Cytogenetic Mapping of *DMI1*, *DMI2*, and *DMI3* Genes of *Medicago truncatula* Involved in Nod factor Transduction, Nodulation, and Mycorrhization" *MPMI* 15 (11): 1108-1118.
Boisson-Dernier, Aurélien et al. (2001) "*Agrobacterium rhizogenes*-Transformed Roots of *Medicago truncatula* for the Study of Nitrogen-Fixing and Endomycorrhizal Symbiotic Associations" *MPMI* 14(6): 695-700.
Bornberg-Bauer, Erich et al. (1998) "Computational approaches to identify leucine zippers" *Nucleic Acids Research* 26 (11): 2740-2746.
Catoira, R., et al. (Sep. 2000) "Four Genes Of *Medicago truncatula* Controlling Components of a Nod Factor Transduction Pathway" *The Plant Cell* 12:1647-1665.
Cook, Douglas R. (1999) "*Medicago truncatula*- a model in the making!" *Current Opinion in Plant Biology* 2: 301-304.
Cullimore, Julie V. et al. (Jan. 2001) "Perception of lipo-chitooligosaccharidic Nod factors in legumes" *TRENDS in Plant Science* 6 (1): 24-30.
Dé narié, Jean et al. (1996) "Rhizobium Lipo-Chitooligosaccharide Nodulation Factors: Signaling Molecules Mediating Recognition and Morphogenesis" *Annu. Rev. Biochem.* 65: 503-35.
Den Hartog, Martine et al. (2001) "Nod factor-induced phosphatidic acid and diacylglycerol pyrophosphate formation: a role for phospoluipase C and D in root hair deformation" *The Plant Journal* 25 (1): 55-65.
Endre, Gabriella et al. (Jun. 27, 2002) "A receptor kinase gene regulating symbiotic nodule development" *Nature* 417: 962-966.
Etzler, Marilynn et al. (May 1999) "A nod factor binding lectin with a pyrase activity from legume roots" *PNAS USA* 96: 5856-5861.
Geurts, René and Ton Bisseling (2002) "*Rhizobium* Nod Factor Perception and Signalling" *The Plant Cell* Supplement: S239-249.
Gressent, Frederic et al. (Apr. 1999) "Ligand spwcificity of a high-affinity binding site for lipo-chitoologosaccharidic Nod factors in *Medicago* cell suspension cultures" *Proc. Natl. Acad. Sci. USA* 96: 4704-4709.
Heckman, Daniel S. et al, (Aug. 10, 2001) "Molecular Evidence for the Early Colonization of Land by Fungi and Plants" *Science* 293: 1129-1133.

(Continued)

Primary Examiner—Medina A. Ibrahim
(74) Attorney, Agent, or Firm—Morrison & Foerster LLP

(57) ABSTRACT

The invention relates to isolated DMI11 genes from *Medicago truncatula* which play a major role both in the early steps of Nod factor signaling that trigger several key developmental responses in the host plant and in the establishment of mycorrhizal symbiosis. The invention also relates to transgenic plants and plant cells expressing the DMI1 protein for increased root nodulation, and methods for transforming plants with a *M. truncatula* DMI1 gene.

17 Claims, 7 Drawing Sheets

OTHER PUBLICATIONS

Jiang, Youxing et al. (May 1, 2003) "X-ray structure of a voltage-dependent K+ channel" *Nature* 423:33-41.

Limpens, Erik et al. (Aug. 28, 2003) "LysM Domain Receptor Kinases Regulating Rhizobial Nod Factor-Induced Infection" *Sciencexpress*. Accessed Jan. 16, 2004 from the World Wide Web at: http://www.sciencemag.org/cgi/content/full/1090074/DC1.

Long, Sharon R. (Oct. 1996) "Rhizobium Symbiosis: Nod Factors in Perspective" *The Plant Cell* 8: 1885-1898.

Madsen, Esben Bjørn et al. (Oct. 9, 2003) "A receptor kinase gene of the LysM type is involved in legume perception of rhizobial signals" *Nature* 425; 637-640.

Mäser, Pascal et al. (Apr. 30, 2002) "Glycine residues in potassium channel-like selectively filters determine potassium selectivity in four-loop-per-subunit HKT transporters from plants" *PNAS* 99 (9):6428-6433.

McKnight, Thomas D. et al. (2002) "Telomeres, telomerase, and stability of the plant genome" *Plant Molecular Biology* 48: 331-337.

Nam, Y.-W. et al. (1999) "Construction of a bacterial artificial chromosome library of *Medicago truncatula* and identification of clones containing ethylene-response genes" *Theor Appl Genet* 98:638-646.

Nielsen, Henrik et al. (1997) "Identification of prokaryotic and eukaryotic signal peptides and prediction of their cleavage sites" *Protein Engineering* 10 (1): 1-6.

Novák, K. (2003) "Allelic Relationships of Pea Nodulation Mutants" *Journal of Heredity* 94 (2): 191-193.

Oldroyd, Giles E.D. and Sharon R. Long (Mar. 2003) "Identification and Characterization of *Nodulation-Signaling Pathway* 2, a Gene of *Medicago truncatula* Involved in Nod Factor Signaling" *Plant Physiology* 131: 1027-1032.

Parniske, Martin and J. Allen Downie (Oct. 9, 2003) "Locks, keys and symbioses" *Nature* 425:569-570.

Penmetsa, R. V., et al. (Aug. 2000) "Production and Characterization of Diverse Developmental Mutants of *Medicago truncatula*[1]" *Plant Physiology* 123: 1387-1397.

Penmetsa, Ramachandra Vanna (Dec. 1998) "Development of a Genetic System in *Medicago truncatula* Production and Characteristics of Developmental and Symbiotic Mutants" Dissertation, Texas A&M University: 107 pages.

Pingret, Jean-Luc et al. (May 1998) "*Rhizobium* Nod Factor Signaling: Evidence for a G Protein-Mediated Transduction Mechanism" *The Plant Cell* 10: 659-671.

Radutoiu, Simona et al. (Oct. 9, 2003) "Plant recognition of symbiotic bacteria requires two LysM receptor-like kinases" *Nature* 425: 585-592.

Sagan, Muriel et al. (1995) "Selection of nodulation and mycorrhizal mutants in the model plant *Medicago truncatula* (Gaertn.) after γ-ray mutagenesis" *Plant Science* 111: 63-71.

Schultze, M. and A. Kondorosi (1998) "Regulation of Symbiotic Root Nodule Development" *Annu. Rev. Genet.* 32: 33-57.

Stracke, Silke et al. (Jun. 27, 2002) "A plant receptor-like kinase required for both bacterial and fungal symbiosis" *Nature* 417: 959-962.

Thoquet, Phillippe et al. (Jun. 2, 2002) "The molecular genetic linkage map of the model legume *Medicago truncatula*: an essential tool for comparative legume genomics and the isolation of agronomically important genes" *BMC Plant Biology* 2:1 (13 pages).

Wais, R. J., et al. (Nov. 2000) "Genetic Analysis of Calcium Spiking Responses in Nodulation Mutants of *Medicago truncatula*" PNAS 97: 13407-13412.

**Nucleic Acid sequence of DMI1 of *M. truncatula*:**
atggcaaagagcaatgaagaatcatcgaatctgaatgtgatgaacaaaccacctttgaagaagacaaag
acacttccttccctcaatctcagagtttctgttactcctcccaatcccaatgacaacaatggaattggaggaactt
caactactaaaactgatttctcagaacaacaatggaactacccttctttccttggcattggcagcacctccaga
aaaagaagacaaccacccctcctccttccaaacctcctgtaaacctcattcctcctcatccccgtccctctc
cgtcaacgaccacaacaaaaccacctcctcacttcttccacaaccttcctcttcctccatcaccaaacaacaa
caacaacactctacctcctctcccatcttctatcttttagttatctgttgtattattcttgtaccctattcagcttatttac
aatacaaacttgccaaactcaaggatatgaaacttcaactctgtggtcaaattgattttgttcccgtaacggaa
aaacatccatacaagaagaggttgatgacgatgataatgcagatagtagaacaatagctttatatattgtgctt
ttcacattgattttgccttttgtattgtacaaatatcttgattatcttcctcaaataattaatttcttgaggagaacaga
aagtaacaaggaggatgtaccattaaagaagagagttgcttatatggtagatgtatttttctccatatatccttat
gcaaagctacttgcacttctttgtgcaactctctttcttatagcatttggtggtttagcgttgtatgcggttactggtgg
tagcatggctgaagcactttggcattcttggacttatgtagctgacgcaggaaatcacgctgaaacagaagg
aaccggccagagaatcgtctctgtctcaattagtgcgggtggcatgcttatatttgccatgatgcttggcttgttt
cggatgctatatcagagaaggttgattcacttagaaaaggaaagagcgaagtcatcgaaagaaaccatgt
actcatccttggctggagtgacaaattgggctcacttttgaagcagctagcaatagccaataagagtgttggtg
gtggtgttattgtggtgcttgcagaaaaggaaaaggaggaaatggaaatggatattgcaaagctcgaattcg
atttcatggggacatcagtaatatgtagaagtggcagtccactaatacttgctgacctaaagaaggtttcagttt
caaaggcacgtgcaatcattgttttagctgcggacgaaaatgcagatcagaaacttattcttagtcagtgttttc
ctcgaatttgtctccagagtgatgcacgtgctttgagagttgttcttagcttagctggtgtaaaggagggcttaag
ggggcatgttgttgtagagatgagcgacctagacaatgaaccccctagtgaaacttgttggtggagaactcatt
gaaacagttgttgcacatgatgtgattggacgtttgatgattcagtgtgctctacagcctggccttgcacagatat
gggaggacattctaggatttgagaatgctgagttttacataaaaagatggcctgaactggatgatcttcttttca
aagacatattaatttcatttcctgatgcaataccgtgtggagttaaggttgctgcagatggagggaagattgtca
taaatccagatgataattatgttctgagagatggtgatgaagtccttgttatagctgaggatgatgacacttatgc
cccaggccctctgccagaggtacgcaagggttatttccctaggatacgtgatcccctaaatatccagagaa
gatactgttttgtggctggcgccgtgacattgatgatatgatcatggttttagaagcattcttggcccctggttcag
aactttggatgttcaatgaagttcctgaaaaggaaagagagaggaaacttgctgctggtgaacttgatgttttg
gattagagaacataaagcttgttcaccggggagggaaatgctgtcattaggcggcacctcgagagtcttcctt
ggagacttttgattctatccttattcttgcagatgagtcagtggaggactctgttgctcattctgactcaagatccct
agccactcttctgctcattcgtgatatacagtcgagacgtctaccttaccgagatacgaagtcaacttctttaac
gttatctgggttctctcataactcatggatccgcgaaatgcaacaagcttcagataaatcaattataattagatc
agtgattatgtattatccatatgagctggttagcatggcactagctatggtagctgaagacaagcagatcaacc
gtgttcttgaggaattatttgcggaggaggggaacgagatgtgtattaagccagcagagttctatttatttgacc
aggaggagctctgtttctatgatataatgattaggggtcgtacaagaaaggagattgttataggctatcgcctg
gccaaccaagagcgtgctattatcaaccctttcagaaaaatctgtgccaagaaaatggtcccttgatgatgtttt
tgttgttttagcctcaggtgaatga (The full sequence is SEQ ID NO: 11)(SEQ ID NO: 13 is underlined).

Figure 6 amino acid sequence of DMI1 gene product:

1 MAKSNEESSNLNVMNKPPLKKTKTLPSLNLRVSVTPPNDNNGIGGTSTTKTDFSEQQW
61 NYPSFLGIGSTSRKRRQPPPPSKPPVNLIPPHPRPLSVNDHNKTTSSLLPQPSSSSITK
121 QQQQHSTSSPIFYLLVICCIILVPYSAYLQYKLAKLKDMKLQLCGQIDFCSRNGKTSIQE
181 EVDDDDNADSRTIALYIVLFTLILPFVLYKYLDYLPQIINFLRRTESNKEDVPLKKRVAY
241 MVDVFFSIYPYAKLLALLCATLFLIAFGGLALYAVTGGSMAEALWHSWTYVADAGNHAET
301 EGTGQRIVSVSISAGGMLIFAMMLGLVSDAISEKVDSLRKGKSEVIERNHVLILGWSDKL
361 GSLLKQLAIANKSVGGGVIVVLAEKEEMEMDIAKLEFDFMGTSVICRSGSPLILADLK
421 KVSVSKARAIIVLAADENADQKLILSQCFPRICLQSDARALRVVLSLAGVKEGLRGHVVV
481 EMSDLDNEPLVKLVGGELIETVVAHDVIGRLMIQCALQPGLAQIWEDILGFENAEFYIKR
541 WPELDDLLFKDILISFPDAPCGVKVAADGGKIVINPDDNYVLRDGDEVLVIAEDDDTYA
601 PGPLPEVRKGYFPRIRDPPKYPEKILFCGWRRDIDDMIMVLEAFLAPGSELWMFNEVPEK
661 ERERKLAAGELDVFGLENIKLVHREGNAVRRHLESLPLETFDSILILADESVEDSVAHS
721 DSRSLATLLIRDIQFLYPGSVIMYYPYELVSMALAMVAEDKQINRVLEELFAEEGNEMC
781 IKPAEFYLFDQEELCFYDIMRGRTRKEIVIGYRLANQERAIINPSEKSVPRKWSLDDVF
841 VVLASGE (The full sequence is SEQ ID NO: 12)(SEQ ID NO: 14 is underlined).

SEQUENCE LISTING

<160> NUMBER OF SEQ ID NOS: 14

<210> SEQ ID NO 1
<211> LENGTH: 554
<212> TYPE: PRT
<213> ORGANISM: Arabidopsis thaliana

<400> SEQUENCE: 1

```
Ser Phe His Arg Ser Leu Ser Leu His Ser Leu Pro Leu Gly Gly Ile
1               5                   10                  15

Lys Ser Ser Ser Phe Arg Gly Thr Phe Lys Val Lys Ser Gln Arg Thr
            20                  25                  30

Gly Asp Thr Glu Pro Pro Asn Lys Asn Phe Lys Asp Leu Asn Ser Lys
        35                  40                  45

Phe Tyr Lys Ser Leu Pro Tyr Lys Leu Val Ile Gly Cys Ile Pro Leu
    50                  55                  60

Tyr Ala Val Leu Arg Ile Ala Gln Lys Ile Phe Gln Glu Leu Pro Asn
65                  70                  75                  80

Leu Ile Gln Asn Ser Val Lys Ala Gly Leu Pro Phe Ala Cys Ala Ser
                85                  90                  95

Asn Ala Ile Asp Lys His Pro Leu Leu Lys Ala Ile Pro Ser Ser His
            100                 105                 110

Asp Ile Lys Trp Gly Leu Ala Arg Ser Ser Tyr Leu Phe Asn Thr Gln
        115                 120                 125

Leu Glu Lys Asn Leu Gly Thr Val Phe Val Val Leu Leu Ile Thr Cys
    130                 135                 140

Phe Ser Phe Val Ile Ile Gly Gly Leu Phe Phe Phe Lys Phe Arg Lys
145                 150                 155                 160

Asp Thr Ser Leu Glu Asp Cys Leu Trp Glu Ala Trp Ala Cys Leu Val
                165                 170                 175

Asn Ala Asp Thr His Leu Glu Gln Lys Thr Arg Phe Glu Arg Leu Ile
            180                 185                 190

Gly Phe Val Leu Ala Ile Trp Gly Ile Val Phe Tyr Ser Arg Leu Leu
        195                 200                 205

Ser Thr Met Thr Glu Gln Phe Arg Tyr His Met Lys Lys Val Arg Glu
    210                 215                 220

Gly Ala His Met Gln Val Leu Glu Ser Asp His Ile Ile Ile Cys Gly
225                 230                 235                 240
```

```
Ile Asn Ser His Leu Pro Phe Ile Leu Lys Gln Leu Asn Ser Tyr Gln
            245                 250                 255

Gln His Ala Val Arg Leu Gly Thr Thr Thr Ala Arg Lys Gln Thr Leu
            260                 265                 270

Leu Leu Met Ser Asp Thr Pro Arg Lys Glu Met Asp Lys Leu Ala Glu
            275                 280                 285

Ala Tyr Ala Lys Asp Phe Asp Gln Leu Asp Ile Leu Thr Lys Ser Cys
            290                 295                 300

Ser Leu Asn Met Thr Lys Ser Phe Glu Arg Ala Ala Cys Met Ala
305                 310                 315                 320

Arg Ala Ile Ile Ile Leu Pro Thr Lys Gly Asp Arg Tyr Glu Val Asp
            325                 330                 335

Thr Asp Ala Phe Leu Ser Val Leu Ala Leu Glu Pro Ile Gln Lys Met
            340                 345                 350

Glu Ser Ile Pro Thr Ile Val Glu Val Ser Ser Asn Met Tyr Asp
            355                 360                 365

Leu Leu Lys Ser Ile Ser Gly Leu Lys Val Glu Pro Val Glu Asn Ser
            370                 375                 380

Thr Ser Lys Leu Phe Val Gln Cys Ser Arg Gln Lys Asp Leu Ile Lys
385                 390                 395                 400

Ile Tyr Arg His Leu Leu Asn Tyr Ser Lys Asn Val Phe Asn Leu Cys
            405                 410                 415

Ser Phe Pro Asn Leu Thr Gly Met Lys Tyr Arg Gln Leu Arg Leu Gly
            420                 425                 430

Phe Gln Glu Val Val Cys Gly Ile Leu Arg Asp Gly Lys Val Asn
            435                 440                 445

Phe His Pro Asn Asp Asp Glu Glu Leu Met Glu Thr Asp Lys Leu Leu
            450                 455                 460

Phe Ile Ala Pro Leu Lys Lys Asp Phe Leu Tyr Thr Asp Met Lys Thr
465                 470                 475                 480

Glu Asn Met Thr Val Asp Glu Thr Asp Asp Thr Arg Lys Gln Val Tyr
            485                 490                 495

Glu Glu Lys Lys Ser Arg Leu Glu Lys Ile Ile Thr Arg Pro Ser Lys
            500                 505                 510

Ser Leu Ser Lys Gly Ser Asp Ser Phe Lys Gly Pro Lys Glu Ser Ile
            515                 520                 525

Leu Leu Leu Gly Trp Arg Gly Asp Val Val Asn Met Ile Lys Glu Phe
            530                 535                 540

Asp Ser Tyr Leu Gly Pro Gly Ser Ser Leu
545                 550

<210> SEQ ID NO 2
<211> LENGTH: 557
<212> TYPE: PRT
<213> ORGANISM: Arabidopsis thaliana

<400> SEQUENCE: 2

Ser Phe Asn Arg Ser Leu Ser Leu Lys Ser Leu Pro Leu Gly Gly Ile
1               5                   10                  15

Gly Ser Phe Arg Cys Pro Gly Thr Phe Lys Val Lys Ser Gln Arg Thr
            20                  25                  30

Gly Asp Thr Glu Pro Ser Ser Val Asn Leu Asn Asp Phe Ser Ser
            35                  40                  45

Ile Leu His Lys Ser Leu Pro Tyr Lys Val Val Ile Gly Cys Ile Pro
50                  55                  60
```

-continued

```
Leu Tyr Ala Val Phe Arg Ile Ala Gln Lys Ile Cys Gln Glu Leu Pro
 65                  70                  75                  80

Arg Leu Val Gln Asn Ser Val Gly Ala Gly Leu Pro Phe Ala Cys Ala
                 85                  90                  95

Ser Asn Ser Leu Pro Thr Pro Leu Lys Leu Asp Val Ser Phe Pro Ser
            100                 105                 110

Phe Gln Asp Ile Arg Trp Gly Leu Ala Arg Phe Leu Tyr Leu Phe Asn
        115                 120                 125

Ile Gln Leu Glu Lys Asn Ile Gly Thr Phe Leu Val Ala Leu Met Ile
    130                 135                 140

Ala Cys Val Ser Phe Val Ile Ile Gly Gly Leu Leu Phe Phe Lys Phe
145                 150                 155                 160

Arg Lys Asp Leu Pro Leu Glu Asp Cys Leu Trp Glu Ala Trp Ala Cys
                165                 170                 175

Leu Ile Ser Ser Ser Thr His Leu Lys Gln Lys Thr Arg Ile Glu Arg
            180                 185                 190

Val Ile Gly Phe Val Leu Ala Ile Trp Gly Ile Leu Phe Tyr Ser Arg
        195                 200                 205

Leu Leu Ser Thr Met Thr Glu Gln Phe Arg Tyr Asn Met Thr Lys Leu
    210                 215                 220

Arg Glu Gly Ala Gln Met Gln Val Leu Glu Ala Asp His Ile Ile Ile
225                 230                 235                 240

Cys Gly Ile Asn Ser His Leu Pro Phe Ile Leu Lys Gln Leu Asn Ser
                245                 250                 255

Tyr His Glu His Ala Val Arg Leu Gly Thr Ala Thr Ala Arg Lys Gln
            260                 265                 270

Arg Leu Leu Leu Met Ser Asp Thr Pro Arg Lys Gln Met Asp Lys Leu
        275                 280                 285

Ala Glu Ala Tyr Ser Lys Asp Phe Asn His Ile Asp Ile Leu Thr Lys
    290                 295                 300

Ser Cys Ser Leu Asn Leu Thr Lys Ser Phe Glu Arg Ala Ala Ala Ser
305                 310                 315                 320

Met Ala Arg Ala Ile Ile Ile Leu Pro Thr Lys Gly Asp Arg Tyr Glu
                325                 330                 335

Val Asp Thr Asp Ala Phe Leu Ser Val Leu Ala Leu Gln Pro Ile Gln
            340                 345                 350

Lys Met Glu Ser Ile Pro Thr Ile Val Glu Val Ser Ser Pro Asn Thr
        355                 360                 365

Tyr Asp Leu Leu Lys Ser Ile Ser Gly Leu Lys Val Glu Pro Val Glu
    370                 375                 380

Asn Val Thr Ser Lys Leu Phe Val Gln Cys Ser Arg Gln Lys Asp Leu
385                 390                 395                 400

Ile Lys Ile Tyr Arg His Leu Leu Asn Tyr Ser Lys Asn Val Phe Asn
                405                 410                 415

Leu Cys Ser Phe Pro Asn Leu Val Gly Thr Lys Tyr Arg Gln Leu Arg
            420                 425                 430

Leu Gly Phe Gln Glu Val Val Cys Gly Leu Leu Arg Asp Gly Lys
        435                 440                 445

Val Asn Phe His Pro Asn Asp Asn Glu Glu Leu Met Glu Thr Asp Lys
    450                 455                 460

Leu Leu Phe Ile Ala Pro Leu Asn Trp Lys Lys Lys Gln Leu Leu Tyr
465                 470                 475                 480
```

```
Thr Asp Met Lys Leu Glu Asn Ile Thr Val Pro Thr Asp Thr Arg Lys
                485                 490                 495

Gln Val Phe Glu Lys Lys Arg Ser Arg Leu Ser Lys Ile Ile Met Arg
            500                 505                 510

Pro Arg Lys Ser Leu Ser Lys Gly Ser Asp Ser Val Lys Gly Pro Thr
            515                 520                 525

Glu Ser Ile Leu Leu Gly Trp Arg Gly Asp Val Val Gln Met Ile
        530                 535                 540

Glu Glu Phe Asp Asn Tyr Leu Gly Pro Gly Ser Ser Met
545                 550                 555

<210> SEQ ID NO 3
<211> LENGTH: 581
<212> TYPE: PRT
<213> ORGANISM: Oryza sativa

<400> SEQUENCE: 3

Ala Leu Pro Leu Ala Leu Arg Phe His Ala Phe Pro Gly Gln Val Arg
 1               5                  10                  15

Val Tyr Arg Gly Gly Gly Ile Gly Val Gly Val Arg Ser Ala Gly His
            20                  25                  30

Leu Pro Ser Lys Arg Gly Leu Val Arg Val Phe Asp Ser Ala Met Gly
        35                  40                  45

Met Asn Glu Lys Val Thr Asn Gly Asn Leu Glu Gln Pro Thr Thr Ser
 50                  55                  60

Thr Ser Gly Asn Asn Pro Ser Phe Pro Ala Glu Gly Asn Phe Asn Val
65                   70                  75                  80

Val Thr Val Val Ser Ile Thr Phe Cys Val Leu His Lys Ile Val Ile
                85                  90                  95

Gly Gln Met Gln Leu Met Thr Lys Phe Leu Pro Trp Met Ser His Asn
            100                 105                 110

Ile Thr Ser Leu Pro Leu Ala Cys Ile Ser Asp Pro Met Lys Lys Pro
        115                 120                 125

Val Pro Leu Lys Leu Asp Val Ser Phe Pro Gln Leu Pro Asp Ile Arg
    130                 135                 140

Trp Ser Ile Ser Arg Leu Tyr Tyr Leu Phe Asn Ser Gln Leu Glu Arg
145                 150                 155                 160

Asn Ile Ala Leu Ser Ile Ile Thr Leu Met Ile Thr Cys Phe Ser Leu
                165                 170                 175

Val Val Val Gly Gly Phe Leu Phe His Lys Phe Arg Lys Asn Gln Gln
            180                 185                 190

Ser Leu Glu Glu Cys Phe Trp Glu Ala Trp Ala Cys Leu Ile Ser Ser
        195                 200                 205

Ser Thr His Leu Arg Gln Lys Thr Arg Ile Glu Arg Val Leu Gly Phe
    210                 215                 220

Phe Leu Ala Ile Trp Gly Ile Leu Phe Tyr Ser Arg Leu Leu Ser Ala
225                 230                 235                 240

Thr Thr Glu Gln Phe Arg Ile Gln Met His Lys Val Arg Glu Gly Ala
                245                 250                 255

Gln Gln Gln Val Ile Glu Asp Asp His Ile Ile Ile Cys Gly Val Asn
            260                 265                 270

Ser His Leu Pro Ser Ile Leu Asn Gln Leu Asn Lys Phe His Glu Ser
        275                 280                 285

Ser Ile Arg Leu Gly Thr Ala Thr Ala Arg Lys Gln Arg Ile Leu Leu
    290                 295                 300
```

-continued

Leu Ser Asp Leu Pro Arg Lys Gln Ile Glu Lys Leu Gly Asp Ser Phe
305                 310                 315                 320

Ala Lys Asp Leu Asn His Ile Asp Val Phe Thr Lys Ser Cys Ser Leu
            325                 330                 335

Ser Leu Thr Lys Ser Phe Glu Arg Ala Ala Asn Lys Ala Lys Ser
        340                 345                 350

Ile Ile Ile Leu Pro Ala Lys Asn Glu Arg Tyr Glu Val Asp Thr Asp
            355                 360                 365

Ala Phe Leu Ser Leu Leu Ala Leu Gln Ser Leu Pro Gln Ile Ala Ser
370                 375                 380

Ile Pro Thr Ile Val Glu Ala Ser Asn Ser Thr Thr Cys Asp Leu Leu
385                 390                 395                 400

Lys Ser Ile Thr Gly Leu Asn Val Gln Pro Val Glu Met Ala Ala Ser
            405                 410                 415

Lys Leu Phe Val Gln Cys Ser Arg Gln Lys Glu Asn Val Phe Asn Leu
            420                 425                 430

Phe Ser Phe Arg Glu Val Val Gly Met Lys Tyr Val Asp Val Arg Arg
            435                 440                 445

Arg Ile Pro Asp Ala Val Val Cys Gly Ile Phe Arg Ser Gly Met Met
        450                 455                 460

His Phe His Pro Cys Glu Asp Glu Val Leu Thr Glu Lys Asp Lys Leu
465                 470                 475                 480

Leu Leu Ile Ala Pro Val Ser Trp Arg Arg Ala Gln Ser Thr Phe
            485                 490                 495

Ser Asn Ser Pro Asn Gly Ala Gln Asn Ser Ser His Tyr Ser Glu Ser
            500                 505                 510

Thr Glu Gly Gln Arg Ser Ser Met Ala Leu Glu Val Asn Glu Thr
        515                 520                 525

Arg Leu Asn Ser Ile Arg Lys Arg Pro Ser Lys Thr Leu Ser Lys Ser
530                 535                 540

Asn Asp Tyr Thr Leu Gly Pro Arg Glu His Val Leu Ile Val Gly Trp
545                 550                 555                 560

Arg Pro Lys Val Thr Asp Met Ile Arg Glu Tyr Asp Asn Tyr Leu Gly
            565                 570                 575

Pro Gly Ser Val Leu
            580

<210> SEQ ID NO 4
<211> LENGTH: 512
<212> TYPE: PRT
<213> ORGANISM: Arabidopsis thaliana

<400> SEQUENCE: 4

Gln Ser Pro Ser Gln Arg Ile Thr Arg Leu Trp Thr Gln Phe Ser Leu
1               5                   10                  15

Thr His Cys Leu Lys Phe Ile Cys Ser Cys Ser Phe Thr Tyr Val Met
            20                  25                  30

Phe Leu Arg Ser Lys Val Ser Arg Leu Glu Ala Glu Asn Ile Ile Leu
        35                  40                  45

Leu Thr Arg Cys Asn Ser Ser Asp Asn Asn Glu Met Glu Glu Thr
    50                  55                  60

Asn Ser Arg Ala Val Val Phe Ser Val Ile Ile Thr Phe Val Leu
65                  70                  75                  80

Pro Phe Leu Leu Tyr Met Tyr Leu Asp Asp Leu Ser His Val Lys Asn

-continued

```
                    85                  90                  95
Leu Leu Arg Arg Thr Asn Gln Lys Lys Glu Asp Val Pro Leu Lys Lys
                100                 105                 110
Arg Leu Ala Tyr Ser Leu Asp Val Cys Phe Ser Val Tyr Pro Tyr Ala
                115                 120                 125
Lys Leu Leu Ala Leu Leu Ala Thr Val Val Leu Ile Val Tyr Gly
            130                 135                 140
Gly Leu Ala Leu Tyr Ala Val Ser Asp Cys Gly Val Asp Glu Ala Leu
145                 150                 155                 160
Trp Leu Ser Trp Thr Phe Val Ala Asp Ser Gly Ser His Ala Asp Arg
                165                 170                 175
Val Gly Val Gly Ala Arg Ile Val Ser Val Ala Ile Ser Ala Gly Gly
            180                 185                 190
Met Leu Ile Phe Ala Thr Met Leu Gly Leu Ile Ser Asp Ala Ile Ser
            195                 200                 205
Lys Met Val Asp Ser Leu Arg Lys Gly Lys Ser Glu Val Leu Glu Ser
210                 215                 220
Asn His Ile Leu Ile Leu Gly Trp Ser Asp Lys Leu Gly Ser Leu Leu
225                 230                 235                 240
Lys Gln Leu Ala Ile Ala Asn Lys Ser Ile Gly Gly Val Val Val
                245                 250                 255
Val Leu Ala Glu Arg Asp Lys Glu Glu Met Glu Thr Asp Ile Ala Lys
                260                 265                 270
Phe Glu Phe Asp Leu Met Gly Thr Ser Val Ile Cys Arg Ser Gly Ser
            275                 280                 285
Pro Leu Ile Leu Ala Asp Leu Lys Lys Val Ser Val Ser Asn Ala Arg
            290                 295                 300
Ala Ile Ile Val Leu Gly Ser Asp Glu Asn Ala Asp Gln Ser Asp Ala
305                 310                 315                 320
Arg Ala Leu Arg Val Val Leu Ser Leu Thr Gly Val Lys Glu Gly Trp
                325                 330                 335
Lys Gly His Val Val Val Glu Met Cys Asp Leu Asp Asn Glu Pro Leu
                340                 345                 350
Val Lys Leu Val Gly Gly Glu Arg Ile Glu Thr Val Val Ala His Asp
            355                 360                 365
Val Ile Gly Arg Leu Met Ile Gln Cys Ala Leu Gln Pro Gly Leu Ala
            370                 375                 380
Gln Ile Trp Glu Asp Ile Leu Gly Phe Glu Asn Ala Glu Phe Tyr Ile
385                 390                 395                 400
Lys Lys Trp Pro Gln Leu Asp Gly Tyr Cys Phe Glu Asp Val Leu Ile
                405                 410                 415
Ser Phe Pro Asn Ala Ile Pro Cys Gly Val Lys Val Ala Ala Asp Gly
                420                 425                 430
Lys Ile Val Leu Asn Pro Ser Asp Asp Tyr Val Leu Lys Glu Gly Asp
            435                 440                 445
Glu Ile Leu Val Ile Ala Glu Asp Asp Thr Tyr Ala Pro Gly Ser
            450                 455                 460
Leu Pro Glu Val Arg Met Cys His Phe Pro Lys Met Gln Asp Pro Pro
465                 470                 475                 480
Lys Tyr Pro Glu Lys Ile Leu Phe Cys Gly Trp Arg Arg Asp Ile Asp
                485                 490                 495
Asp Met Ile Lys Val Leu Glu Ala Leu Leu Ala Pro Gly Ser Glu Leu
            500                 505                 510
```

<210> SEQ ID NO 5
<211> LENGTH: 529
<212> TYPE: PRT
<213> ORGANISM: Medicago truncatula

<400> SEQUENCE: 5

```
Leu Leu Pro Gln Pro Ser Ser Ser Ile Thr Lys Gln Gln Gln Gln
 1               5                  10                  15

His Ser Thr Ser Ser Pro Ile Phe Tyr Leu Leu Val Ile Cys Cys Ile
            20                  25                  30

Ile Leu Val Pro Tyr Ser Ala Tyr Leu Gln Tyr Lys Leu Ala Lys Leu
        35                  40                  45

Lys Asp Met Lys Leu Gln Leu Cys Gly Gln Ile Asp Phe Cys Ser Arg
50                  55                  60

Asn Gly Lys Thr Ser Ile Gln Glu Glu Val Asp Asp Asp Asn Ala
65                  70                  75                  80

Asp Ser Arg Thr Ile Ala Leu Tyr Ile Val Leu Phe Thr Leu Ile Leu
                85                  90                  95

Pro Phe Val Leu Tyr Lys Tyr Leu Asp Tyr Leu Pro Gln Ile Ile Asn
            100                 105                 110

Phe Leu Arg Arg Thr Glu Ser Asn Lys Glu Asp Val Pro Leu Lys Lys
        115                 120                 125

Arg Val Ala Tyr Met Val Asp Val Phe Phe Ser Ile Tyr Pro Tyr Ala
130                 135                 140

Lys Leu Leu Ala Leu Leu Cys Ala Thr Leu Phe Leu Ile Ala Phe Gly
145                 150                 155                 160

Gly Leu Ala Leu Tyr Ala Val Thr Gly Gly Ser Met Ala Glu Ala Leu
                165                 170                 175

Trp His Ser Trp Thr Tyr Val Ala Asp Ala Gly Asn His Ala Glu Thr
            180                 185                 190

Glu Gly Thr Gly Gln Arg Ile Val Ser Val Ser Ile Ser Ala Gly Gly
        195                 200                 205

Met Leu Ile Phe Ala Met Met Leu Gly Leu Val Ser Asp Ala Ile Ser
210                 215                 220

Glu Lys Val Asp Ser Leu Arg Lys Gly Lys Ser Glu Val Ile Glu Arg
225                 230                 235                 240

Asn His Val Leu Ile Leu Gly Trp Ser Asp Lys Leu Gly Ser Leu Leu
                245                 250                 255

Lys Gln Leu Ala Ile Ala Asn Lys Ser Val Gly Gly Val Ile Val
            260                 265                 270

Val Leu Ala Glu Lys Glu Lys Glu Glu Met Glu Met Asp Ile Ala Lys
        275                 280                 285

Leu Glu Phe Asp Phe Met Gly Thr Ser Val Ile Cys Arg Ser Gly Ser
290                 295                 300

Pro Leu Ile Leu Ala Asp Leu Lys Lys Val Ser Val Ser Lys Ala Arg
305                 310                 315                 320

Ala Ile Ile Val Leu Ala Ala Asp Glu Asn Ala Asp Gln Ser Asp Ala
                325                 330                 335

Arg Ala Leu Arg Val Val Leu Ser Leu Ala Gly Val Lys Glu Gly Leu
            340                 345                 350

Arg Gly His Val Val Val Glu Met Ser Asp Leu Asp Asn Glu Pro Leu
        355                 360                 365

Val Lys Leu Val Gly Gly Glu Leu Ile Glu Thr Val Val Ala His Asp
```

```
                370                 375                 380
Val Ile Gly Arg Leu Met Ile Gln Cys Ala Leu Gln Pro Gly Leu Ala
385                 390                 395                 400

Gln Ile Trp Glu Asp Ile Leu Gly Phe Glu Asn Ala Glu Phe Tyr Ile
                405                 410                 415

Lys Arg Trp Pro Glu Leu Asp Leu Leu Phe Lys Asp Ile Leu Ile
                420                 425                 430

Ser Phe Pro Asp Ala Ile Pro Cys Gly Val Lys Val Ala Ala Asp Gly
                435                 440                 445

Gly Lys Ile Val Ile Asn Pro Asp Asp Asn Tyr Val Leu Arg Asp Gly
450                 455                 460

Asp Glu Val Leu Val Ile Ala Glu Asp Asp Thr Tyr Ala Pro Gly
465                 470                 475                 480

Pro Leu Pro Glu Val Arg Lys Gly Tyr Phe Pro Arg Ile Arg Asp Pro
                485                 490                 495

Pro Lys Tyr Pro Glu Lys Ile Leu Phe Cys Gly Trp Arg Arg Asp Ile
                500                 505                 510

Asp Asp Met Ile Met Val Leu Glu Ala Phe Leu Ala Pro Gly Ser Glu
                515                 520                 525

Leu
```

```
<210> SEQ ID NO 6
<211> LENGTH: 533
<212> TYPE: PRT
<213> ORGANISM: Oryza sativa

<400> SEQUENCE: 6

Arg Glu Glu Glu Lys Ser Leu Ala Ser Val Val Lys Arg Pro Met Leu
1               5                   10                  15

Leu Asp Glu Arg Arg Ser Leu Ser Pro Pro Pro Gln Gln Arg Ala
            20                  25                  30

Pro Arg Phe Asp Leu Ser Pro Tyr Leu Val Leu Met Leu Val Val Thr
        35                  40                  45

Val Ile Ser Phe Ser Leu Ala Ile Trp Gln Trp Met Lys Ala Thr Val
50                  55                  60

Leu Gln Glu Lys Ile Arg Ser Cys Cys Ser Val Ser Thr Val Asp Cys
65                  70                  75                  80

Lys Thr Thr Thr Glu Ala Phe Lys Ile Asn Gly Gln His Gly Ser Asp
                85                  90                  95

Phe Ile Asn Ser Ala Asp Trp Asn Leu Ala Ser Cys Ser Arg Met Leu
            100                 105                 110

Val Phe Ala Ile Pro Val Phe Leu Val Lys Tyr Ile Asp Gln Leu Arg
        115                 120                 125

Arg Arg Asn Thr Asp Ser Ile Arg Leu Arg Ser Thr Glu Glu Glu Val
    130                 135                 140

Pro Leu Lys Lys Arg Ile Ala Tyr Lys Val Asp Val Phe Ser Gly
145                 150                 155                 160

His Pro Tyr Ala Lys Leu Leu Ala Leu Leu Ala Thr Ile Ile Leu
                165                 170                 175

Ile Ala Ser Gly Gly Ile Ala Leu Tyr Val Val Ser Gly Ser Gly Phe
            180                 185                 190

Leu Glu Ala Leu Trp Leu Ser Trp Thr Phe Val Ala Asp Ser Gly Asn
        195                 200                 205

His Ala Asp Gln Val Gly Leu Gly Pro Arg Ile Val Ser Val Ser Ile
```

```
            210                 215                 220
Ser Ser Gly Gly Met Leu Val Phe Ala Thr Met Leu Gly Leu Val Ser
225                 230                 235                 240

Asp Ala Ile Ser Glu Lys Val Asp Ser Trp Arg Lys Gly Lys Ser Glu
            245                 250                 255

Gly Ser Leu Leu Lys Gln Leu Ala Ile Ala Asn Lys Ser Ile Gly Gly
            260                 265                 270

Gly Val Val Val Leu Ala Glu Arg Asp Lys Glu Met Glu Met
        275                 280                 285

Asp Ile Gly Lys Leu Glu Phe Asp Phe Met Gly Thr Ser Val Ile Cys
        290                 295                 300

Arg Ser Gly Ser Pro Leu Ile Leu Ala Asp Leu Lys Lys Val Ser Val
305                 310                 315                 320

Ser Lys Ala Arg Ala Ile Ile Val Leu Ala Ser Asp Glu Asn Ala Asp
            325                 330                 335

Gln Ser Asp Ala Arg Ala Leu Arg Val Val Leu Ser Leu Thr Gly Val
            340                 345                 350

Lys Glu Gly Leu Arg Gly His Val Val Glu Met Ser Asp Leu Asp
        355                 360                 365

Asn Glu Pro Leu Val Lys Leu Val Gly Gly Glu Leu Ile Glu Thr Val
        370                 375                 380

Val Ala His Asp Val Ile Gly Arg Leu Met Ile Gln Cys Ala Leu Gln
385                 390                 395                 400

Pro Gly Leu Ala Gln Ile Trp Glu Asp Ile Leu Gly Phe Glu Asn Ala
            405                 410                 415

Glu Phe Tyr Ile Lys Arg Trp Pro Glu Leu Asp Gly Met Arg Phe Gly
            420                 425                 430

Asp Val Leu Ile Ser Phe Pro Asp Ala Val Pro Cys Gly Val Lys Ile
            435                 440                 445

Ala Ser Lys Ala Gly Lys Ile Leu Met Asn Pro Asn Asp Tyr Val
        450                 455                 460

Leu Gln Glu Gly Asp Glu Val Leu Val Ile Ala Glu Asp Asp Thr
465                 470                 475                 480

Tyr Val Pro Ala Ser Leu Pro Gln Val Arg Lys Gly Phe Leu Pro Asn
            485                 490                 495

Ile Pro Thr Pro Pro Lys Tyr Pro Glu Lys Ile Leu Phe Cys Gly Trp
        500                 505                 510

Arg Arg Asp Ile His Asp Met Ile Met Val Leu Glu Ala Phe Leu Ala
            515                 520                 525

Pro Gly Ser Glu Leu
        530

<210> SEQ ID NO 7
<211> LENGTH: 416
<212> TYPE: PRT
<213> ORGANISM: Streptomyces avermitilis

<400> SEQUENCE: 7

Met Glu Arg Ser Lys Asp Arg Arg Pro Val Ser Leu Gln Asp Arg Ala
1               5                   10                  15

Arg Tyr Trp Phe Asp Arg Thr Leu Ala Arg Ser Thr Gly Thr Leu Met
            20                  25                  30

Gly Trp Leu Val Ile Ile Cys Leu Ala Val Val Pro Val Ser Ala
        35                  40                  45
```

-continued

```
Leu Leu Val Trp Thr Asp Pro Gly Ser Pro Arg Ser Leu Ser Gly Arg
 50                  55                  60

Leu Ala Ala Val Trp Arg Ser Ser Ala Glu Thr Leu Arg Leu Gly Thr
 65                  70                  75                  80

Val Thr Gly Thr Pro Leu Arg Met Leu Leu Ser Ala Leu Leu Gly Leu
                 85                  90                  95

Val Ala Leu Leu Cys Val Ser Thr Leu Val Gly Val Ile Thr Thr Gly
                100                 105                 110

Leu Ala Glu Arg Leu Ala Glu Leu Ser Arg Gly Arg Ser Thr Val Leu
            115                 120                 125

Glu Gln Gly His Ala Val Leu Gly Trp Ser Asp Gln Val Ser Thr
130                 135                 140

Val Val Gly Glu Leu Val Ala Ala Gln Ser Ser Tyr Arg Pro Arg Ala
145                 150                 155                 160

Val Val Val Leu Ala Glu Arg Asp Lys Thr Glu Met Glu Arg Ala Leu
                165                 170                 175

Ala Ala His Val Gly Pro Ala Gly Arg Thr Arg Leu Val Cys Arg Ser
                180                 185                 190

Gly Pro Ala Ser Asp Pro Gly Val Leu Ala Leu Val Ser Pro Gln Thr
            195                 200                 205

Ala Ser Thr Val Leu Val Leu Pro Ser Gly Glu Pro Thr Ala Asp Ala
210                 215                 220

Glu Val Leu Arg Val Leu Leu Ala Leu Arg Ala Val Leu Gly Glu Gly
225                 230                 235                 240

Thr Gly Gly Pro Pro Val Leu Ala Ala Val Leu Asp Asp Arg Tyr Arg
                245                 250                 255

Ala Pro Ala Arg Leu Ala Ala Gly Pro Arg Gly Thr Val Leu Glu Thr
                260                 265                 270

Asp Thr Val Thr Ala Arg Leu Ile Ala Gln Cys Val Gly Arg Pro Gly
            275                 280                 285

Leu Ser Leu Val Leu Arg Asp Leu Leu Asp Phe Ala Gly Asp Glu Phe
290                 295                 300

His Leu Ala Glu Ala Thr Ala Phe His Gly Gly Pro Phe Gly Ala Ala
305                 310                 315                 320

Leu Leu Gly His Ala Thr Ser Cys Val Val Gly Leu Leu Thr Ala Glu
                325                 330                 335

Gly Arg Thr Leu Leu Asn Pro Pro Ala Ala Thr Leu Val Ala Pro Gly
                340                 345                 350

Ser Arg Leu Val Val Leu Thr Arg Asp Asp Gly Ser Ala Arg Pro Glu
            355                 360                 365

Asp Cys Arg His Leu Val Glu Pro Ser Ala Ile Ala Met Ala Gln Pro
370                 375                 380

Pro Pro Glu Asp Ala Ala His Leu Leu Leu Leu Gly Trp Asn Arg Arg
385                 390                 395                 400

Ala Pro Leu Val Val Asn Gln Leu Arg Arg Thr Ala Arg Pro Gly Ser
                405                 410                 415
```

<210> SEQ ID NO 8
<211> LENGTH: 55
<212> TYPE: PRT
<213> ORGANISM: Streptomyces griseus

<400> SEQUENCE: 8

```
Met Thr Thr Ala Pro Gly Ser Arg Thr Ala Ala Ile Ser Ser Thr Pro
 1               5                  10                  15
```

```
Arg Asp Arg Pro Ser Arg Pro Glu Pro Asp Asp Pro Ser Arg Leu Leu
        20                  25                  30

Leu Leu Gly Trp Asn Arg Arg Ala Pro Leu Val Leu Asp Gln Leu Arg
        35                  40                  45

Ser Thr Ala Arg Thr Gly Ser
    50                  55

<210> SEQ ID NO 9
<211> LENGTH: 412
<212> TYPE: PRT
<213> ORGANISM: Streptomyces coelicolor

<400> SEQUENCE: 9

Met Gly Arg Arg Arg Ala Val Ser Trp Gln His Arg Ala Arg Tyr Ala
 1               5                  10                  15

Phe Asp Arg Thr Leu Ala Arg Ser Thr Gly Ala Leu Leu Gly Trp Leu
                20                  25                  30

Ala Ala Cys Cys Leu Ala Ile Val Val Pro Val Ser Thr Leu Leu Val
        35                  40                  45

Trp Thr Asp Pro Arg Ala Pro Arg Ser Leu Thr Glu Arg Leu Val Ala
    50                  55                  60

Val Trp Arg Thr Ser Ala Glu Thr Leu Arg Leu Gly Val Thr Gly
 65                  70                  75                  80

Ala Pro Leu Arg Met Leu Leu Ser Val Phe Leu Gly Leu Ile Ala Leu
                85                  90                  95

Leu Cys Val Ser Thr Leu Val Gly Val Ile Thr Thr Gly Leu Gly Asp
               100                 105                 110

Arg Leu Glu Glu Leu Arg Arg Gly Arg Ser Arg Val Leu Glu Lys Gly
           115                 120                 125

His Ala Val Val Leu Gly Trp Ser Asp Gln Val Phe Thr Val Val Gly
       130                 135                 140

Glu Met Val Ile Ser Gln Val Gly Arg Val Arg Gly Ala Val Ala Val
145                 150                 155                 160

Leu Ala Asp Arg Asp Ser Ala Val Met Ala Ser Asp Leu Asn Ala Ala
                165                 170                 175

Leu Gly Val Thr Arg Gly Val Arg Val Val Cys Arg Thr Gly Ala Pro
            180                 185                 190

Ile Asp Pro Ala Ala Leu Ala Leu Leu Thr Pro Ala Ala His Cys
        195                 200                 205

Val Leu Val Leu Pro Gly Asp Asp Ala Asp Ala Glu Val Val
    210                 215                 220

Arg Val Leu Leu Ala Leu Arg Ala Leu Leu Gly Ala Gly Ala Gly Pro
225                 230                 235                 240

Pro Val Ala Ala Val Arg Asp Glu Arg Phe Leu Thr Ala Ala Arg
                245                 250                 255

Leu Ala Ala Gly Pro Arg Gly Phe Val Leu Asp Val Glu Ser Thr Ala
            260                 265                 270

Ala Arg Leu Leu Val Gln Ala Ala Arg His Pro Gly Leu Val Arg Ala
        275                 280                 285

Leu Arg Asp Leu Leu Asp Leu Thr Gly Ala Glu Phe His Val Val His
    290                 295                 300

Ala Pro Asp Ala Leu Gly Leu Thr Phe Ala Glu Ile Ser Ser Arg Tyr
305                 310                 315                 320

Glu Glu Ala Cys Ala Val Gly Tyr Leu Ala Ala Asp Gly Arg Ala Leu
```

```
                   325                 330                 335
Leu Thr Pro Ala Ser Gly Ala Arg Cys Gly Pro Gly Asp Arg Leu Ile
                340                 345                 350

Val Val Ala Arg Asp Asp Arg Pro Val Ala Lys Arg Glu Gly Thr
            355                 360                 365

Ala Val Asp Pro Thr Val Met Ala Asp Arg Pro Asp Arg Gln Arg Ser
        370                 375                 380

Phe Ser Lys Thr Leu Leu Gly Trp Asn Arg Arg Ala Pro Leu Val
385                 390                 395                 400

Met Glu Ser Leu Ser Arg Thr Ala Gln Pro Gly Ser
                405                 410

<210> SEQ ID NO 10
<211> LENGTH: 414
<212> TYPE: PRT
<213> ORGANISM: Mesorhizobium loti

<400> SEQUENCE: 10

Met Lys Lys Arg Asp Ser Leu Gly Thr Arg Leu Arg Tyr Gly Phe Asp
1               5                   10                  15

Lys Ser Met Ala Ala Gly Pro Ile Ala Leu Ile Gly Trp Leu Ala Val
                20                  25                  30

Val Ser Leu Leu Ile Ile Ala Ala Ala Phe Leu Ala Val Thr
            35                  40                  45

Arg Ile Ala Pro Glu Gly Gly Glu Pro Leu Asn Phe Phe Glu Ala Phe
        50                  55                  60

Trp Glu Ser Leu Met Arg Thr Leu Asp Ser Gly Thr Met Gly Gly Asp
65              70                  75                  80

Thr Gly Trp Ala Phe Arg Leu Val Met Leu Val Thr Leu Ala Gly
                85                  90                  95

Ile Phe Val Val Ser Ala Leu Ile Gly Val Leu Ser Ala Gly Val Asp
            100                 105                 110

Gly Lys Leu Asp Glu Leu Arg Lys Gly Arg Ser Arg Val Leu Glu Ser
            115                 120                 125

Asp His Thr Ile Ile Leu Asn Trp Ser Pro Ser Ile Phe Asp Val Ile
            130                 135                 140

Ser Glu Leu Val Ile Ala Asn Ala Ser Arg Arg Pro Arg Ile Val
145                 150                 155                 160

Val Met Ala Asn Met Asp Lys Val Ala Met Glu Asp Glu Ile Ala Ala
                165                 170                 175

Lys Val Gly Lys Leu Gly Asn Thr Arg Ile Ile Cys Arg Ser Gly Asp
            180                 185                 190

Pro Thr Asp Leu Tyr Asp Leu Ala Ile Val Asn Pro Gln Thr Ser Arg
        195                 200                 205

Ser Val Ile Val Leu Ser Pro Asp Gly Asp Pro Asp Ser Gln Val
    210                 215                 220

Ile Lys Thr Val Leu Ala Leu Val Asn Asp Pro Ser Arg Arg Thr Asp
225                 230                 235                 240

Pro Tyr Asn Ile Ala Ala Glu Ile Arg Asp Gly Lys Asn Ala Glu Val
                245                 250                 255

Ala Arg Val Val Gly Gly Ala Glu Val Gln Leu Val Leu Ala Asp Gln
            260                 265                 270

Leu Ile Ser Arg Ile Val Val His Ser Ser Arg Gln Ser Gly Leu Ser
        275                 280                 285
```

-continued

| | | | | | | | | | | | |
|---|---|---|---|---|---|---|---|---|---|---|---|
|Gly|Val|Tyr|Ser|Glu|Leu|Leu|Asp|Phe|Asp|Gly|Cys|Glu|Ile|Tyr|Thr|
| |290| | | |295| | | |300| | | | | | |

Thr Thr Gln Pro Glu Leu Ala Gly Lys Thr Phe Gly Glu Ala Val Met
305                 310                 315                 320

Ala Tyr Glu His Cys Ala Leu Ile Gly Leu Cys Asp Gln Gly Gly Arg
                325                 330                 335

Val Asn Leu Asn Pro Pro Ser Glu Leu Val Ile Gly Lys Asp Met Arg
            340                 345                 350

Ala Ile Ile Ile Ala Glu Asp Asp Ala Ala Ile Arg Pro Gly Ser Ala
        355                 360                 365

Gly Ile Lys Ile Asp Thr Ala Ala Ile Arg Asp Pro Arg Pro Val Glu
    370                 375                 380

Ala Lys Pro Glu Arg Thr Leu Ile Leu Gly Trp Asn Arg Arg Gly Pro
385                 390                 395                 400

Ile Ile Thr Tyr Glu Leu Ser Arg Tyr Val Ala Pro Gly Ser
                405                 410

<210> SEQ ID NO 11
<211> LENGTH: 2646
<212> TYPE: DNA
<213> ORGANISM: Medicago truncatula

<400> SEQUENCE: 11

```
atggcaaaga gcaatgaaga atcatcgaat ctgaatgtga tgaacaaacc acctttgaag      60
aagacaaaga cacttccttc cctcaatctc agagtttctg ttactcctcc caatcccaat     120
gacaacaatg gaattggagg aacttcaact actaaaactg atttctcaga caacaatgg      180
aactaccctt ctttccttgg cattggcagc acctccagaa aagaagaca accaccccct      240
cctccttcca aacctcctgt aaacctcatt cctcctcatc cccgtcccct ctccgtcaac     300
gaccacaaca aaaccacctc ctcacttctt ccacaacctt cctcttcctc catcaccaaa     360
caacaacaac aacactctac ctcctctccc atcttctatc ttttagttat ctgttgtatt     420
attcttgtac cctattcagc ttatttacaa tacaaacttg ccaaactcaa ggatatgaaa     480
cttcaactct gtggtcaaat tgatttttgt tcccgtaacg gaaaaacatc catacaagaa     540
gaggttgatg acgatgataa tgcagatagt agaacaatag ctttatatat tgtgcttttc     600
acattgattt tgcctttgt attgtacaaa tatcttgatt atcttcctca ataattaat      660
ttcttgagga gaacagaaag taacaaggag gatgtaccat aaagaagag agttgcttat      720
atggtagatg tattttctc catatatcct tatgcaaagc tacttgcact tctttgtgca      780
actctcttc ttatagcatt tggtggttta gcgttgtatg cggttactgg tggtagcatg      840
gctgaagcac tttggcattc ttggacttat gtagctgacg caggaaatca cgctgaaaca      900
gaaggaaccg gccagagaat cgtctctgtc tcaattagtg cgggtggcat gcttatattt      960
gccatgatgc ttgggcttgt ttcggatgct atatcagaga aggttgattc acttagaaaa     1020
ggaaagagcg aagtcatcga agaaaccat gtactcatcc ttggctggag tgacaaattg     1080
ggctcacttt tgaagcagct agcaatagcc aataagagtg ttggtggtgg tgttattgtg     1140
gtgcttgcag aaaaggaaaa ggaggaaatg gaaatggata ttgcaaagct cgaattcgat     1200
ttcatgggga catcagtaat atgtagaagt ggcagtccac taatacttgc tgacctaaag     1260
aaggtttcag tttcaaaggc acgtgcaatc attgttttag ctgcggacga aaatgcagat     1320
cagaaactta ttcttagtca gtgttttcct cgaatttgtc tccagagtga tgcacgtgct     1380
ttgagagttg ttcttagctt agctggtgta aaggagggct aagggggca tgttgttgta     1440
```

```
gagatgagcg acctagacaa tgaaccccta gtgaaacttg ttggtggaga actcattgaa    1500
acagttgttg cacatgatgt gattggacgt ttgatgattc agtgtgctct acagcctggc    1560
cttgcacaga tatgggagga cattctagga tttgagaatg ctgagtttta cataaaaga     1620
tggcctgaac tggatgatct tcttttcaaa gacatattaa tttcatttcc tgatgcaata    1680
ccgtgtggag ttaaggttgc tgcagatgga gggaagattg tcataaatcc agatgataat    1740
tatgttctga gagatggtga tgaagtcctt gttatagctg aggatgatga cacttatgcc    1800
ccaggccctc tgccagaggt acgcaagggt tatttcccta ggatacgtga tccccctaaa    1860
tatccagaga agatactgtt ttgtggctgg cgccgtgaca ttgatgatat gatcatggtt    1920
ttagaagcat tcttggcccc tggttcagaa ctttggatgt tcaatgaagt tcctgaaaag    1980
gaaagagaga ggaaacttgc tgctggtgaa cttgatgttt ttggattaga aacataaag     2040
cttgttcacc gggagggaaa tgctgtcatt aggcggcacc tcgagagtct tcctttggag    2100
acttttgatt ctatccttat tcttgcagat gagtcagtgg aggactctgt tgctcattct    2160
gactcaagat ccctagccac tcttctgctc attcgtgata tacagtcgag acgtctacct    2220
taccgagata cgaagtcaac ttctttaacg ttatctgggt tctctcataa ctcatggatc    2280
cgcgaaatgc aacaagcttc agataaatca attataatta gatcagtgat tatgtattat    2340
ccatatgagc tggttagcat ggcactagct atggtagctg aagacaagca gatcaaccgt    2400
gttcttgagg aattatttgc ggaggagggg aacgagatgt gtattaagcc agcagagttc    2460
tatttatttg accaggagga gctctgtttc tatgatataa tgattagggg tcgtacaaga    2520
aaggagattg ttataggcta tcgcctggcc aaccaagagc gtgctattat caaccccttca   2580
gaaaaatctg tgccaagaaa atggtccctt gatgatgttt tgttgttttt agcctcaggt    2640
gaatga                                                                 2646
```

<210> SEQ ID NO 12
<211> LENGTH: 847
<212> TYPE: PRT
<213> ORGANISM: Medicago truncatula

<400> SEQUENCE: 12

```
Met Ala Lys Ser Asn Glu Glu Ser Ser Asn Leu Asn Val Met Asn Lys
 1               5                  10                  15

Pro Pro Leu Lys Lys Thr Lys Thr Leu Pro Ser Leu Asn Leu Arg Val
            20                  25                  30

Ser Val Thr Pro Pro Asn Pro Asn Asp Asn Asn Gly Ile Gly Gly Thr
        35                  40                  45

Ser Thr Thr Lys Thr Asp Phe Ser Glu Gln Gln Trp Asn Tyr Pro Ser
    50                  55                  60

Phe Leu Gly Ile Gly Ser Thr Ser Arg Lys Arg Gln Pro Pro
65                  70                  75                  80

Pro Pro Ser Lys Pro Pro Val Asn Leu Ile Pro Pro His Pro Arg Pro
                85                  90                  95

Leu Ser Val Asn Asp His Asn Lys Thr Thr Ser Ser Leu Leu Pro Gln
            100                 105                 110

Pro Ser Ser Ser Ile Thr Lys Gln Gln Gln Gln His Ser Thr Ser
        115                 120                 125

Ser Pro Ile Phe Tyr Leu Leu Val Ile Cys Cys Ile Ile Leu Val Pro
    130                 135                 140

Tyr Ser Ala Tyr Leu Gln Tyr Lys Leu Ala Lys Leu Lys Asp Met Lys
```

```
                                -continued
145                 150                 155                 160
Leu Gln Leu Cys Gly Gln Ile Asp Phe Cys Ser Arg Asn Gly Lys Thr
                165                 170                 175
Ser Ile Gln Glu Glu Val Asp Asp Asp Asn Ala Asp Ser Arg Thr
            180                 185                 190
Ile Ala Leu Tyr Ile Val Leu Phe Thr Leu Ile Leu Pro Phe Val Leu
                195                 200                 205
Tyr Lys Tyr Leu Asp Tyr Leu Pro Gln Ile Ile Asn Phe Leu Arg Arg
    210                 215                 220
Thr Glu Ser Asn Lys Glu Asp Val Pro Leu Lys Lys Arg Val Ala Tyr
225                 230                 235                 240
Met Val Asp Val Phe Phe Ser Ile Tyr Pro Tyr Ala Lys Leu Leu Ala
                245                 250                 255
Leu Leu Cys Ala Thr Leu Phe Leu Ile Ala Phe Gly Gly Leu Ala Leu
                260                 265                 270
Tyr Ala Val Thr Gly Gly Ser Met Ala Glu Ala Leu Trp His Ser Trp
            275                 280                 285
Thr Tyr Val Ala Asp Ala Gly Asn His Ala Glu Thr Glu Gly Thr Gly
            290                 295                 300
Gln Arg Ile Val Ser Val Ser Ile Ser Ala Gly Gly Met Leu Ile Phe
305                 310                 315                 320
Ala Met Met Leu Gly Leu Val Ser Asp Ala Ile Ser Glu Lys Val Asp
                325                 330                 335
Ser Leu Arg Lys Gly Lys Ser Glu Val Ile Glu Arg Asn His Val Leu
            340                 345                 350
Ile Leu Gly Trp Ser Asp Lys Leu Gly Ser Leu Leu Lys Gln Leu Ala
            355                 360                 365
Ile Ala Asn Lys Ser Val Gly Gly Val Ile Val Leu Ala Glu
            370                 375                 380
Lys Glu Lys Glu Glu Met Glu Met Asp Ile Ala Lys Leu Glu Phe Asp
385                 390                 395                 400
Phe Met Gly Thr Ser Val Ile Cys Arg Ser Gly Ser Pro Leu Ile Leu
                405                 410                 415
Ala Asp Leu Lys Lys Val Ser Val Ser Lys Ala Arg Ala Ile Ile Val
                420                 425                 430
Leu Ala Ala Asp Glu Asn Ala Asp Gln Lys Leu Ile Leu Ser Gln Cys
            435                 440                 445
Phe Pro Arg Ile Cys Leu Gln Ser Asp Ala Arg Ala Leu Arg Val Val
            450                 455                 460
Leu Ser Leu Ala Gly Val Lys Glu Gly Leu Arg Gly His Val Val Val
465                 470                 475                 480
Glu Met Ser Asp Leu Asp Asn Glu Pro Leu Val Lys Leu Val Gly Gly
            485                 490                 495
Glu Leu Ile Glu Thr Val Val Ala His Asp Val Ile Gly Arg Leu Met
            500                 505                 510
Ile Gln Cys Ala Leu Gln Pro Gly Leu Ala Gln Ile Trp Glu Asp Ile
            515                 520                 525
Leu Gly Phe Glu Asn Ala Glu Phe Tyr Ile Lys Arg Trp Pro Glu Leu
            530                 535                 540
Asp Asp Leu Leu Phe Lys Asp Ile Leu Ile Ser Phe Pro Asp Ala Ile
545                 550                 555                 560
Pro Cys Gly Val Lys Val Ala Ala Asp Gly Gly Lys Ile Val Ile Asn
                565                 570                 575
```

-continued

```
Pro Asp Asp Asn Tyr Val Leu Arg Asp Gly Asp Glu Val Leu Val Ile
            580                 585                 590
Ala Glu Asp Asp Thr Tyr Ala Pro Gly Pro Leu Pro Glu Val Arg
        595                 600                 605
Lys Gly Tyr Phe Pro Arg Ile Arg Asp Pro Pro Lys Tyr Pro Glu Lys
    610                 615                 620
Ile Leu Phe Cys Gly Trp Arg Arg Asp Ile Asp Asp Met Ile Met Val
625                 630                 635                 640
Leu Glu Ala Phe Leu Ala Pro Gly Ser Glu Leu Trp Met Phe Asn Glu
                645                 650                 655
Val Pro Glu Lys Glu Arg Glu Arg Lys Leu Ala Ala Gly Glu Leu Asp
            660                 665                 670
Val Phe Gly Leu Glu Asn Ile Lys Leu Val His Arg Glu Gly Asn Ala
        675                 680                 685
Val Ile Arg Arg His Leu Glu Ser Leu Pro Leu Glu Thr Phe Asp Ser
    690                 695                 700
Ile Leu Ile Leu Ala Asp Glu Ser Val Glu Asp Ser Val Ala His Ser
705                 710                 715                 720
Asp Ser Arg Ser Leu Ala Thr Leu Leu Leu Ile Arg Asp Ile Gln Phe
                725                 730                 735
Leu Tyr Pro Gly Ser Val Ile Met Tyr Tyr Pro Tyr Glu Leu Val Ser
            740                 745                 750
Met Ala Leu Ala Met Val Ala Glu Asp Lys Gln Ile Asn Arg Val Leu
        755                 760                 765
Glu Glu Leu Phe Ala Glu Gly Asn Glu Met Cys Ile Lys Pro Ala
    770                 775                 780
Glu Phe Tyr Leu Phe Asp Gln Glu Glu Leu Cys Phe Tyr Asp Ile Met
785                 790                 795                 800
Ile Arg Gly Arg Thr Arg Lys Glu Ile Val Ile Gly Tyr Arg Leu Ala
                805                 810                 815
Asn Gln Glu Arg Ala Ile Ile Asn Pro Ser Glu Lys Ser Val Pro Arg
            820                 825                 830
Lys Trp Ser Leu Asp Asp Val Phe Val Leu Ala Ser Gly Glu
        835                 840                 845
```

<210> SEQ ID NO 13
<211> LENGTH: 1050
<212> TYPE: DNA
<213> ORGANISM: Medicago truncatula

<400> SEQUENCE: 13

```
tatccttatg caaagctact tgcacttctt tgtgcaactc tctttcttat agcatttggt     60
ggtttagcgt tgtatgcggt tactggtggt agcatggctg aagcactttg cattcttgg    120
acttatgtag ctgacgcagg aaatcacgct gaaacagaag gaaccggcca gagaatcgtc    180
tctgtctcaa ttagtgcggg tggcatgctt atatttgcca tgatgcttgg gcttgtttcg    240
gatgctatat cagagaaggt tgattcactt agaaaaggaa agagcgaagt catcgaaaga    300
aaccatgtac tcatccttgg ctggagtgac aaattgggct cacttttgaa gcagctagca    360
atagccaata agagtgttgg tggtggtgtt attgtggtgc ttgcagaaaa ggaaaaggag    420
gaaatggaaa tggatattgc aaagctcgaa ttcgatttca tggggacatc agtaatatgt    480
agaagtggca gtccactaat aacttgctga ctaaagaagg tttcagtttc aaaggcacgt    540
gcaatcattg ttttagctgc ggacgaaaat gcagatcaga aacttattct tagtcagtgt    600
```

-continued

```
tttcctcgaa tttgtctcca gagtgatgca cgtgctttga gagttgttct tagcttagct    660
ggtgtaaagg agggcttaag ggggcatgtt gttgtagaga tgagcgacct agacaatgaa    720
cccctagtga aacttgttgg tggagaactc attgaaacag ttgttgcaca tgatgtgatt    780
ggacgtttga tgattcagtg tgctctacag cctggccttg cacagatatg ggaggacatt    840
ctaggatttg agaatgctga gttttacata aaaagatggc ctgaactgga tgatcttctt    900
ttcaaagaca tattaatttc atttcctgat gcaataccgt gtggagttaa ggttgctgca    960
gatggaggga agattgtcat aaatccagat gataattatg ttctgagaga tggtgatgaa   1020
gtccttgtta tagctgagga tgatgacact                                    1050
```

<210> SEQ ID NO 14
<211> LENGTH: 357
<212> TYPE: PRT
<213> ORGANISM: Medicago truncatula

<400> SEQUENCE: 14

```
Met Val Asp Val Phe Phe Ser Ile Tyr Pro Tyr Ala Lys Leu Leu Ala
  1               5                  10                  15

Leu Leu Cys Ala Thr Leu Phe Leu Ile Ala Phe Gly Gly Leu Ala Leu
             20                  25                  30

Tyr Ala Val Thr Gly Gly Ser Met Ala Glu Ala Leu Trp His Ser Trp
         35                  40                  45

Thr Tyr Val Ala Asp Ala Gly Asn His Ala Glu Thr Glu Gly Thr Gly
     50                  55                  60

Gln Arg Ile Val Ser Val Ser Ile Ser Ala Gly Met Leu Ile Phe
 65                  70                  75                  80

Ala Met Met Leu Gly Leu Val Ser Asp Ala Ile Ser Glu Lys Val Asp
                 85                  90                  95

Ser Leu Arg Lys Gly Lys Ser Glu Val Ile Glu Arg Asn His Val Leu
            100                 105                 110

Ile Leu Gly Trp Ser Asp Lys Leu Gly Ser Leu Leu Lys Gln Leu Ala
        115                 120                 125

Ile Ala Asn Lys Ser Val Gly Gly Val Ile Val Val Leu Ala Glu
    130                 135                 140

Lys Glu Lys Glu Glu Met Glu Met Asp Ile Ala Lys Leu Glu Phe Asp
145                 150                 155                 160

Phe Met Gly Thr Ser Val Ile Cys Arg Ser Gly Ser Pro Leu Ile Leu
                165                 170                 175

Ala Asp Leu Lys Lys Val Ser Val Ser Lys Ala Arg Ala Ile Ile Val
            180                 185                 190

Leu Ala Ala Asp Glu Asn Ala Asp Gln Lys Leu Ile Leu Ser Gln Cys
        195                 200                 205

Phe Pro Arg Ile Cys Leu Gln Ser Asp Ala Arg Ala Leu Arg Val Val
    210                 215                 220

Leu Ser Leu Ala Gly Val Lys Glu Gly Leu Arg Gly His Val Val Val
225                 230                 235                 240

Glu Met Ser Asp Leu Asp Asn Glu Pro Leu Val Lys Leu Val Gly Gly
                245                 250                 255

Glu Leu Ile Glu Thr Val Val Ala His Asp Val Ile Gly Arg Leu Met
            260                 265                 270

Ile Gln Cys Ala Leu Gln Pro Gly Leu Ala Gln Ile Trp Glu Asp Ile
        275                 280                 285
```

-continued

```
Leu Gly Phe Glu Asn Ala Glu Phe Tyr Ile Lys Arg Trp Pro Glu Leu
    290                 295                 300

Asp Asp Leu Leu Phe Lys Asp Ile Leu Ile Ser Phe Pro Asp Ala Ile
305                 310                 315                 320

Pro Cys Gly Val Lys Val Ala Ala Asp Gly Gly Lys Ile Val Ile Asn
                325                 330                 335

Pro Asp Asp Asn Tyr Val Leu Arg Asp Gly Asp Glu Val Leu Val Ile
                340                 345                 350

Ala Glu Asp Asp Asp
            355
```

DMI1 GENE ENCODES A PROTEIN THAT IS REQUIRED FOR THE EARLY STEPS OF BACTERIAL AND FUNGAL SYMBIOSES

RELATED APPLICATION

This application claims priority to U.S. Application No. 60/510,098 filed Oct. 8, 2003, which is hereby incorporated by reference herein in its entirety.

GOVERNMENT RIGHTS

This invention was made with Government support under Grant (or Contract) Nos. DE-FG03-98ER20296 and DE-FG03-01ER15200, awarded by the DOE. The Government has certain rights in this invention.

FIELD OF THE INVENTION

This invention is in the field of plant nitrogen fixation and phosphate uptake.

BACKGROUND OF THE INVENTION

Plants require nitrogen, phosphorus and certain other essential elements to survive and grow. Most fertilizers include both nitrogen, in the form of ammonium or nitrates, and phosphorus. However, not all of a fertilizer used in farming is taken up by the crops. A fair amount of the fertilizer is washed away and contaminates the ground water in the surrounding community. In addition, supplementing soil nutrients with fertilizer increases the cost to produce a crop. Nitrogen in the atmosphere represents a good source for nitrogen given its abundance. But only prokaryotes are able to "fix" atmospheric nitrogen into a form usable by plants. Certain plants, legumes in particular, have evolved a symbiotic relationship with nitrogen fixing bacteria. Such plants are often planted to replenish the soils for other crops. In addition, some of the same proteins that are involved in establishing this symbiosis also participate in establishing symbiosis with mycorrhizal fungi that assist in utilization of phosphorus. Thus there is a need for methods of enhancing a plant's symbiotic machinery to reduce the need for supplementing soil with added nutrients. In addition, there is a need for methods and compositions that enhance the nutrients in the soil directly such as addition of bacteria that fix nitrogen in the absence of symbiosis with plants to lower costs associated with fertilizing during farming.

SUMMARY OF THE INVENTION

The present invention meets the needs for enhanced symbiosis in plants and methods and compositions for direct supplementation of soils with nitrogen and/or phosphorus.

Mutations in a genetic locus of the legume plant *Medicago truncatula* resulted in the inability to form root nodules that are produced in wild type *M. truncatula* from interaction with *Sinorhizobium meliloti* (rhizobia). The locus was mapped in the *M. truncatula* genome, and using positional cloning strategies the molecular identity of the gene was identified. In addition to conditioning the ability to allow formation of symbiotic root nodules identified, the gene controls establishment of symbiosis with mycorrhizal fungi.

Together, the rhizobial and mycorrhizal symbioses with legumes constitute key mechanisms by which plants acquire nitrogen and phosphorous. Identifying the genes that control these plant-microbe associations offers the potential for genetic manipulation of these important plant pathways. This invention allows one to control the development of symbiotic organs and tissues in interaction with beneficial bacteria and mycorrhizae. Furthermore, this invention permits genetic engineering of enhanced nitrogen and phosphorous acquisition in plants.

The present invention is directed to the finding that the dmi1 gene controls the ability to establish rhizobial and mycorrhizal symbioses in *Medicago truncatula*. The "dmi1 nucleic acid sequence" as defined herein refers to any sequence that hybridizes to the nucleic acid molecule of SEQ ID NO:11 or the complement thereof under at least low stringency, preferably moderate, high or very high stringency conditions, or is about 85%, 90%, 95%, or 97% identical in the nucleic acid sequence of SEQ ID NO:11, or encodes a polypeptide having at least about 85%, 90%, 95%, or 97% sequence identity to the amino acid sequence of SEQ ID NO:12. This invention is directed to the dmi1 nucleic acid sequence as described above. The invention is further directed to oligonucleotide primers that bind the nucleic acid sequence of SEQ ID NO:11.

The invention is further directed to recombinant constructs containing such isolated nucleic acids. The recombinant constructs may further comprise a promoter. The promoter may be a homologus or a heterologous promoter. The recombinant constructs may further be in a vector. By way of example but not in limitation, the vector may be a cloning, expression, transformation, or transfection vector. The recombinant construct may be introduced into a prokaryotic or eukaryotic host cell. The recombinant construct may be introduced into a plant so that the expression of the nucleic acid may be controlled or regulated. The introduction of the construct into the plant may be transient or stable. The control or regulation may include root-specific promoters designed to express the isolated nucleic acids in roots. Such regulation may be directed to constitutive expression. The regulation may be altered in response to various biotic, abiotic and artificial stimuli, relative to the native dmi1 promoter.

The invention is further directed to isolated nucleic acids encoding the protein depicted in SEQ ID NO:12 and paralogs, homologs and orthologs of the protein. Yet another aspect of the present invention includes DMI1-related proteins and nucleic acids encoding such proteins. The DMI1-related proteins are proteins with structural homology to DMI1 proteins that have at least one DMI1 activity including the ability to regulate mycorrhizal and/or rhizobial symbiosis, the ability to increase available nitrogen and/or phosphorus in a cell or organism, the ability to increase nitrogen and/or phosphorus uptake into a cell or organism and/or the ability to regulate cation levels in or around a cell. Nucleic acids encoding DMI1-related proteins may be in a vector or transgenically expressed in plants. Such nucleic acids are preferably operably linked to a promoter that may be an inducible promoter, a regulated promoter, or a constitutive promoter. The DMI1-related protein coding sequences of the invention include those sequences that hybridize under at least low stringency and preferably moderate, high, or very high stringency conditions to the nucleic acid of SEQ ID NO:11 or its complement. In another embodiment of the presenting invention, the DMI1-related protein coding sequences also include those sequences with at least 85% sequence identity and preferably at least 90%, or at least 95% sequence identity with a nucleotide sequence of SEQ ID NO:11. The present invention also includes isolated proteins having the protein sequence of SEQ ID NO:12 as well as protein sequences with at least 85% sequence identity and preferably at least 90%, or at least 95% sequence identity with the protein sequence of SEQ ID NO:12. The present invention further includes nucleic acid sequences encoding the above protein sequences.

The invention is also directed to antibodies and ligands that bind a polypeptide having at least about 85%, 90%, 95%, or 97% sequence identity to the amino acid sequence of SEQ ID NO:12. The invention is further directed to non-naturally occurring cation channels comprising the nucleic acid that encodes a polypeptide having at least about 85%, 90%, 95%, or 97% sequence identity to the amino acid sequence of SEQ ID NO:P2.

The invention is further directed to transgenic plants containing the isolated nucleic acids of the invention. The invention is further directed to seed produced from the transgenic plants of the invention. The present invention is further directed to methods of enhancing nitrogen and/or phosphorous acquisition in transgenic plants by transforming plants with the nucleic acids of the invention wherein the nucleic acids are operatively linked to a promoter. The invention is directed to a method of increasing root nodulation in a plant. The invention is further directed to use of these transgenic plants to increase available nitrogen in the soil. The invention is also directed to a fertilizer comprising cells or organisms comprising an increased accumulation of nitrogen and/or phosphorus wherein said increase is due to the presence of an exogenous dmi1 nucleic acid sequence.

(A) A comparative genetic map of *M. truncatula* and *M. sativa* was established by reciprocal transfer (arrows) of genetic markers between the two related genomes.

(B) Panel B presents a minimum tiling path of BAC clones covering the DMI1 region. All five BAC clones were sequenced and annotated for candidate genes. The gap between mth2-80I8 and the telomere was filled by PCR and sequenced (Riely et al., manuscript in preparation).

(C) The *Arabidopsis* and *M. truncatula* homologs, but not their rice counterpart (data not shown), reside in a region of conserved genome microsynteny, presumably indicative of the ancestral chromosomal context.

Figure 2:
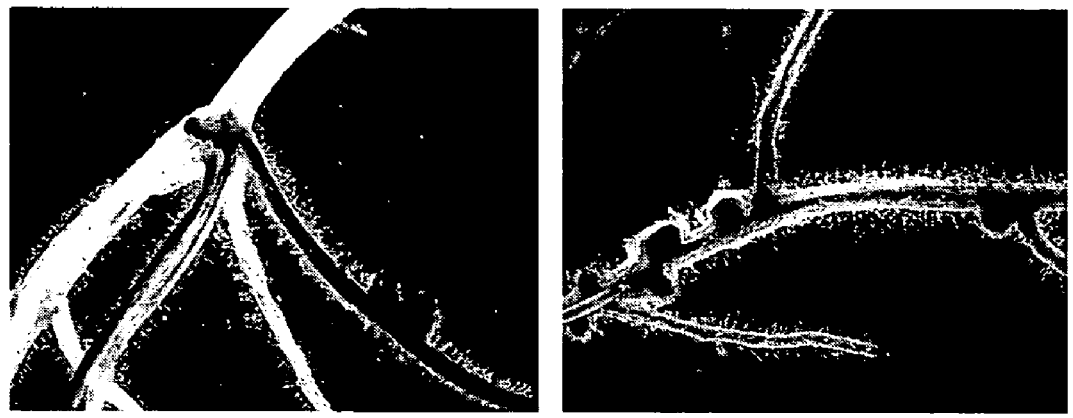

FIG. 2 shows the complementation of the dmi1 phenotype using *A. rhizogenes* based transformation.

Figure 3:
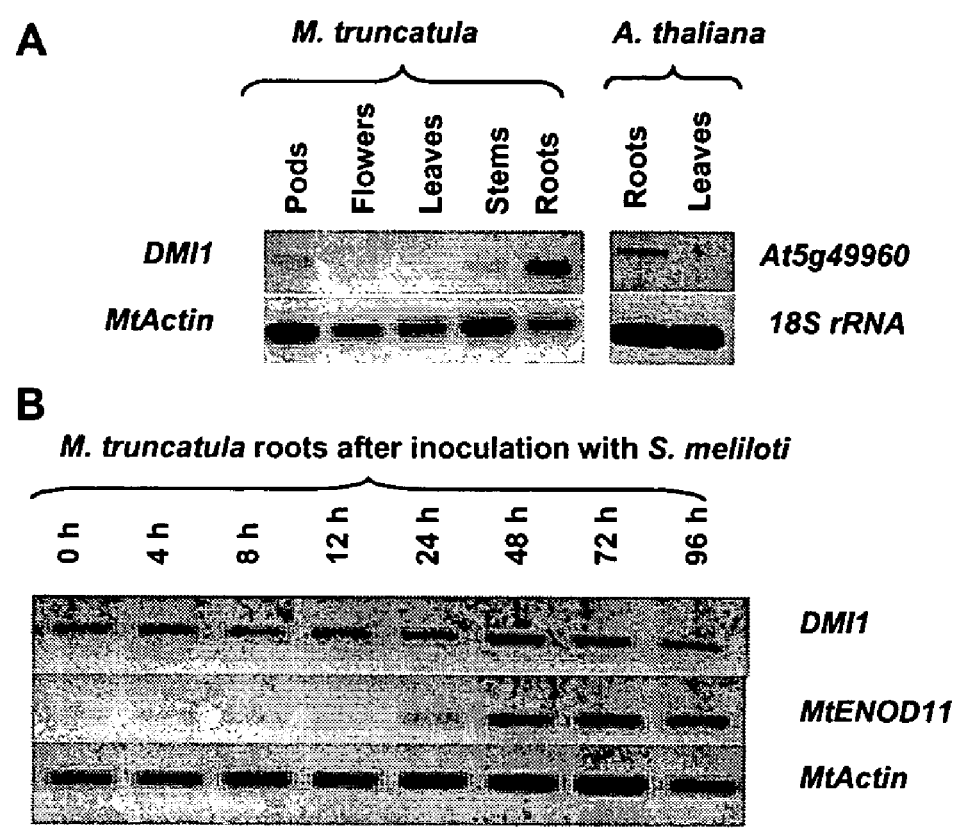

Roots of DMI1 and wild type plants were transformed with either the DMI1 cDNA under control of the native promoter or with vector alone. Transformed roots were inoculated with *Sinorhizobium meliloti* and nodule development was scored visually after 15 days. A constitutively expressed uidA gene was used as a reporter to identify transformed tissues based on GUS staining. Among more than 80 independent DMI1 transformants, only those transformed by the DMI1 transgene were nodulated by *S. meliloti*, while transformation of wild type plants with either DMI1 or control constructs had no effect on nodulation FIG. 3 shows the expression profiles of DMI1 in *M. truncatula* and *A. thaliana*. RNAs were extracted using RNeasy Plant Minikit (Qiagen, Germany) and quantified with Ribogreen RNA quantitation kit (Molecular Probes, USA).

(A) *M. truncatula* DMI1 and *A. thaliana* At5g49960 cDNA analysis by semi-quantitative RT-PCR in different tissues. DMI1 is expressed strongly in roots, but not in aerial tissues of *Medicago truncatula*. The DMI1 ortholog in *Arabidopsis* is expressed in roots but not leaves.

(B) *M. truncatula* DMI1 expression is not altered upon inoculation by wild type *S. meliloti*. RT-PCR experiments were performed using the PowerScript™ RT-PCR kit (Clontech laboratories, USA).

FIG. 4 shows DMI1 proteins and homologs.

(A) Partial alignment of DMI1 homologous proteins sequences by means of ClustalW with default parameters. *A. thaliana* At5g49960 (SEQ ID NO:4) and rice BAB64102 DMI1 (SEQ ID NO:6) orthologs share about 80% similarity with the *M. truncatula* protein (SEQ ID NO:5). *A. thaliana* At5g02940 (SEQ ID NO:1), At5g43735 (SEQ ID NO:2) and rice AAN06856 (SEQ ID NO:3) proteins are 73% similar and share ~37% similarity with the orthologous grouping of DMI1-related proteins in *M. truncatula*, *Arabidopsis* and rice. *Mesorhizobium loti* NP_102608 (SEQ ID NO:10) and the *Streptomyces* (*S. avermitilis* NP821931—SEQ ID NO:7; *S griseus* JL0032—SEQ ID NO:8; *S. coelicolor* NP631245—SEQ ID NO:9) proteins represent a third clade of proteins, with 60% similarity between bacterial homologs and ~37% similarity to the DMI1 orthologs. Transmembrane domains (dark gray) were predicted using THMM, TMpred and TopPred 2 software programs (us.expasy.org/tools/). The presence of signal peptides (underlined) was assessed using SignalP V2.0 software (at the cbs.dtu.dk/services/SignalP-2.0/web site). The region homologous to cation channels was determined according to Anantharaman et al. (12) and annotated according to Jiang et al. (19).

(B) Unrooted phylogenetic tree and schematic diagrams of DMI1 homologs. Full-length protein sequences were aligned using ClustalW with default parameters. The branch-and-bound parsimony method was used to infer phylogenetic relationships, identifying two paralogous groups of plant genes and a single group of bacterial orthologs. Percentage bootstrap support is given to the side of each branch.

FIG. 5 shows the nucleic acid sequence of DMI1 of *M. truncatula*.

FIG. 6 shows the amino acid sequence of the DMI1 gene product.

BRIEF DESCRIPTION OF THE SEQUENCE LISTING

The following sequences are grouped according to the nature of the sequence. The list does not include sequences used as PCR primers or sequences used in sequence comparisons.

SEQ ID NO:11 is the protein encoding nucleotide sequence of DMI1 from the legume *Medicago truncatula*.

SEQ ID NO:13 is the portion of the protein encoding nucleotide sequence of DMI1 from the legume *Medicago truncatula* that is predicted to have cation channel activity as depicted in FIG. 5.

SEQ ID NO:12 is the amino acid sequence of DMI1 from the legume *Medicago truncatula* as depicted in FIG. 6.

SEQ ID NO:14 is the portion of the amino acid sequence of DMI1 from the legume *Medicago truncatula* that is predicted to have cation channel activity as depicted in FIG. 6.

DETAILED DESCRIPTION OF THE INVENTION

Before explaining at least one embodiment of the invention in detail, it is to be understood that the invention is not limited in its application to the details of construction and the arrangement of the components set forth in the following description. The invention is capable of other embodiments or of being practiced or carried out in various ways. Also, it is to be understood that the phraseology and terminology employed herein is for the purpose of description and should not be regarded as limiting.

Throughout this disclosure, various publications, patents and published patent specifications are referenced. The disclosures of these publications, patents and published patent specifications are hereby incorporated by reference into the present disclosure to more fully describe the state of the art to which this invention pertains. The practice of the present invention will employ, unless otherwise indicated, conventional techniques of plant breeding, immunology, molecular biology, microbiology, cell biology and recombinant DNA, which are within the skill of the art. See, e.g., Sambrook, Fritsch and Maniatis, MOLECULAR CLONING: A LABORATORY MANUAL, 2nd edition (1989); CURRENT PROTOCOLS IN MOLECULAR BIOLOGY (F. M. Ausubel, et al. eds., (1987); Plant Breeding: Principles and Prospects (Plant Breeding, Vol 1) M. D. Hayward, N. O. Bosemark, I. Romagosa; Chapman & Hall, (1993.); Coligan, Dunn, Ploegh, Speicher and Wingfeld, eds. (1995) CURRENT PROTOCOLS IN PROTEIN SCIENCE (John Wiley & Sons, Inc.); the series METHODS IN ENZYMOLOGY (Academic Press, Inc.): PCR 2: A PRACTICAL APPROACH (M. J. MacPherson, B. D. Hames and G. R. Taylor eds. (1995), Harlow and Lane, eds. (1988) ANTIBODIES, A LABORATORY MANUAL, and ANIMAL CELL CULTURE R. I. Freshney, ed. (1987).

Unless otherwise noted, technical terms are used according to conventional usage. Definitions of common terms in molecular biology may be found in Lewin, Genes V, published by Oxford University Press, 1994 (SBN 0-19-854287-9); Kendrew et al. (eds.), The Encyclopedia of Molecular Biology, published by Blackwell Science Ltd., 1994 (SBN 0-632-02182-9); and Robert A. Meyers (ed.), Molecular Biology and Biotechnology, a Comprehensive Desk Reference, published by VCH Publishers, Inc., 1995 (ISBN 1-56081-569-8); Ausubel et al. (1987) Current Protocols in Molecular Biology, Green Publishing; Sambrook et al. (1989) Molecular Cloning: A Laboratory Manual, Cold Spring Harbor, N.Y. Definitions of common terms in plant biology may be found in Esau, Plant Anatomy, published by John Wiley & Sons (1977) (ISBN 0-471-24520-8); and Solomon et al., Biology, published by Saunders College Publishing (1993).

Definitions

In order to facilitate review of the various embodiments of the invention, the following definitions are provided:

DMI1 protein or polypeptide, or dmi1 gene: A DMI1 protein or DMI1 polypeptide is a protein encoded by the gene dmi1. In *Medicago truncatula*, mutations in DMI1 result in loss of the ability to form mycorrhizal or rhizobial symbiotic relationships.

The present invention may be practiced using nucleic acid sequences that encode full length DMI1 proteins as well as DMI1-derived proteins that retain DMI1 activity. The preferred DMI1 proteins are legume derived. DMI1-derived proteins which retain DMI1 biological activity include fragments of DMI1, generated either by chemical (e.g. enzymatic) digestion or genetic engineering means; chemically functionalized protein molecules obtained starting with the exemplified protein or nucleic acid sequences, and protein sequence variants, for example allelic variants and mutational variants, such as those produced by in vitro mutagenesis techniques, such as gene shuffling (Stemmer et al., 1994a, 1994b). Thus, the term "DMI1 protein" encompasses full-length DMI1 proteins, as well as such DMI1 derived proteins that retain DMI1 activity. Depending upon the intended use of the DMI1 protein, the DMI1 biological activity may encompass the full activity of the DMI1 protein in mediating the rhizobial and fungus mycorrhizal symbiosis in plants. In certain situations, the DMI biological activity may encompass mediation of only one of the two forms of symbiosis. For example, where the intended utility of the DMI1 protein is related to the enhancement of nitrogen fixation, then the relevant DMI1 biological activity will be the mediation of the rhizobial symbiosis. In still other situations, the DMI1 biological activity will be the cation channel activity.

Representative but non-limiting DMI1 sequences useful in the invention include SEQ ID NO:11, SEQ ID NO:13, SEQ ID NO:12, and SEQ ID NO:14.

Promoter: A regulatory nucleic acid sequence, typically located upstream (5') of a gene or protein coding sequence that, in conjunction with various cellular proteins, is responsible for regulating the expression of the gene or protein coding sequence. The promoters suitable for use in the heterologous nucleic acids of this invention are functional in plants and in other host organisms used for expressing the inventive polynucleotides. Many plant promoters are publicly known. These include constitutive promoters, regulated promoters, inducible promoters, root-, tissue-and cell-specific promoters, and developmentally-regulated promoters. Exemplary promoters and fusion promoters are described, e.g., in WO 02/00894, which is herein incorporated by reference.

The promoters may be those normally associated with a transgene of interest, or heterologous promoters which are derived from genes of other plants, viruses, and plant pathogenic bacteria and fungi. Those skilled in the art will be able without undue experimentation to select promoters that are suitable for use in practicing the subject invention.

Regulated promoter: As used herein, this term refers to any promoter functional in a plant that provides differential expression levels in response to stimuli internal to the plant such as developmental signals. This includes both promoters that increase expression and promoters that decrease expression in response to stimuli or changed external conditions. Many promoters that are regulated promoters are also inducible promoters. For example, promoters that are responsive to auxin are both because they will change levels of expression in response to developmental changes in auxin levels and in response to externally supplied auxin.

Examples of regulated promoters under developmental control include promoters that initiate transcription only, or preferentially, in certain tissues, such as leaves, roots, fruit, seeds, or flowers. Exemplary promoters include the anther specific promoter 5126 (U.S. Pat. Nos. 5,689,049 and 5,689,051), glob-1 promoter, and gamma-zein promoter. An exemplary promoter for leaf-and stalk-preferred expression is MS8-15 (see U.S. Pat. No. 5,986,174, herein incorporated by reference). Examples of seed-preferred promoters included, but are not limited to, 27 kD gamma zein promoter and waxy promoter (Boronat et al. (1986); Reina et al. (1990); and Kloesgen et al. (1986)). Promoters that express in the embryo, pericarp, and endosperm are disclosed in U.S. applications Ser. No. 60/097,233 filed Aug. 20, 1998 and U.S. applications Ser. No. 60/098,230 filed Aug. 28, 1998 both of which are hereby incorporated by reference in their entirety. The operation of a promoter may also vary depending on its location in the genome. Thus, a developmentally regulated promoter may become fully or partially constitutive in certain locations. A developmentally regulated promoter can also be modified, if necessary, for weak expression.

Sequence Identity: Sequences that show similarity to those described in this application can be identified by computer-based methods, using public domain sequence alignment algorithms and sequence similarity search tools to search sequence databases (public domain databases include Genbank, EMBL, Swiss-Prot, PIR and others).

Similarity searches retrieve and align sequences for comparison with a target sequence to be analyzed (i.e., a query sequence). The optimal alignment between local regions of the compared sequences is known as a local alignment. Sequence comparison algorithms use scoring matrices to assign an overall score to each of the alignments.

Polynucleotide and polypeptide sequences may be aligned, and percentage of identical residues in a specified region may be determined against other polynucleotide and polypeptide sequences, using computer algorithms that are publicly available. The percentage identity score is dependent on the length of the overlap region of the sequences being compared.

The similarity between two nucleic acid sequences, or two amino acid sequences may be expressed in terms of sequence identity (or, for proteins, also in terms of sequence similarity). Sequence identity is frequently measured in terms of percentage identity; the higher the percentage, the more similar the two sequences are. Homologs are nucleic acid or amino acid sequences that share a common ancestry as assessed by phylogenetic methods. The term "homolog" does not imply a particular level of similarity, although homologs of recent ancestry are typically more similar than homologs of distant ancestry. Therefore, percent identity or percent similarity may be used as approximate measures of how related a given pair of genes are. We have identified DMI1 homologs throughout the plant kingdom. As described herein, homologs and variants of the DMI1 nucleic acid molecules may be used in the present invention. Closely related homologs and variants of these nucleic acid molecules will possess a relatively high degree of sequence identity when aligned using standard methods. Such homologs and variants will hybridize under high stringency conditions to one another.

Methods of alignment of sequences for comparison are well known in the art. Various programs and alignment algorithms are described in: Smith and Waterman (1981); Needleman and Wunsch (1970); Pearson and Lipman (1988); Higgins and Sharp (1988); Higgins and Sharp (1989); Corpet et al. (1988); Huang et al. (1992); and Pearson et al. (1994). Altschul et al. (1994) presents a detailed consideration of sequence alignment methods and homology calculations.

The NCBI Basic Local Alignment Search Tool (BLAST) (Altschul et al., 1990) is available from several sources, including the National Center for Biotechnology Information (NCBI, Bethesda, Md.) and on the Internet, for use in connection with the sequence analysis programs blastp, blastn, blastx, tblastn and tblastx. It can be accessed at the NCBI Website. A description of how to determine sequence identity using this program is available at the NCBI website.

Homologs of the disclosed protein sequences are typically characterized by possession of at least 40% sequence identity counted over the full length alignment with the amino acid sequence of the disclosed sequence using the NCBI Blast 2.0, gapped blastp set to default parameters. The adjustable parameters are preferably set with the following values: overlap span 1, overlap fraction=0.125, word threshold (T)=11. The HSP S and HSP S2 parameters are dynamic values and are established by the program itself depending upon the composition of the particular sequence and composition of the particular database against which the sequence of interest is being searched; however, the values may be adjusted to increase sensitivity. Proteins with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

Homologs of the disclosed nucleic acid sequences are typically characterized by possession of at least 40% sequence identity counted over the full length alignment with the amino acid sequence of the disclosed sequence using the NCBI Blast 2.0, gapped blastn set to default parameters. In addition, such sequences hybridize to homologous sequences under high stringency conditions. A preferred method utilizes the BLASTN module of WU-BLAST-2 (Altschul et al., 1996); set to the default parameters, with overlap span and overlap fraction set to 1 and 0.125, respectively. Nucleic acid sequences with even greater similarity to the reference sequences will show increasing percentage identities when assessed by this method, such as at least about 50%, at least about 60%, at least about 70%, at least about 75%, at least about 80%, at least about 85%, at least about 90% or at least about 95% sequence identity.

The alignment may include the introduction of gaps in the sequences to be aligned. In addition, for sequences which contain either more or fewer amino acids than the protein depicted in SEQ ID NO:12, it is understood that in one embodiment, the percentage of sequence identity will be determined based on the number of identical amino acids in relation to the total number of amino acids. Thus, for example, sequence identity of sequences shorter than that shown in the figures as discussed below, will be determined using the number of amino acids in the longer sequence, in one embodiment. In percent identity calculations relative weight is not assigned to various manifestations of sequence variation, such as, insertions, deletions, substitutions, etc.

In one embodiment, only identities are scored positively (+1) and all forms of sequence variation including gaps are assigned a value of "0", which obviates the need for a weighted scale or parameters as described herein for sequence similarity calculations. Percent sequence identity can be calculated, for example, by dividing the number of matching identical residues by the total number of residues of the "shorter" sequence in the aligned region and multiplying by 100. The "longer" sequence is the one having the most actual residues in the aligned region.

Proteins can be classified according to their sequence relatedness to other proteins in the same genome (paralogs) or a different genome (orthologs). Ortholog genes are genes that evolved by speciation from a common ancestral gene. These genes normally retain the same function as they evolve. Paralog genes are genes that are duplicated within a genome. These genes may acquire new specificities or modified functions which may be related to the original one. Phylogenetic analysis methods are well-known to those with ordinary skill in bioinformatics.

As will be appreciated by those skilled in the art, the sequences of the present invention may contain sequencing errors. That is, there may be incorrect amino acid sequences, nucleotides, frameshifts, unknown nucleotides, or other types of sequencing errors in any of the sequences; however, the correct sequences will fall within the homology and stringency definitions herein for nucleic acids, and the protein homology described for proteins or polypeptides.

Stringency: Stringency refers to hybridization conditions chosen to optimize binding of polynucleotide sequences with different degrees of complementarity. Stringency is affected by factors such as temperature, salt conditions, the presence of organic solvents in the hybridization mixtures, and the lengths and base compositions of the sequences to be hybridized and the extent of base mismatching, and the combination of parameters is more important than the absolute measure of any one factor.

Very High Stringency: Very high stringency conditions refers to hybridization to filter-bound DNA in 5×SSC, 2% sodium dodecyl sulfate (SDS), 100 μg/ml single stranded DNA at 55–65° C. for 8 hours, and washing in 0.1×SSC and 0.1% SDS at 60–65° C. for thirty minutes.

High Stringency: High stringency conditions refers to hybridization to filter-bound DNA in 5×SSC, 2% sodium dodecyl sulfate (SDS), 100 μg/ml single stranded DNA at 55–65° C. for 8 hours, and washing in 0.2×SSC and 0.2% SDS at 60–65° C. for thirty minutes.

Moderate Stringency: Moderate stringency conditions refers to hybridization to filter-bound DNA in 5×SSC, 2% sodium dodecyl sulfate (SDS), 100 μg/ml single stranded DNA at 55–65° C. for 8 hours, and washing in 0.2×SSC and 0.2% SDS at 50–55° C. for thirty minutes.

Low Stringency: Low stringency conditions refers to hybridization to filter-bound DNA in 5×SSC, 2% sodium dodecyl sulfate (SDS), 100 μg/ml single stranded DNA at 55–65° C. for 8 hours, and washing in 2.0×SSC and 0.2% SDS at 50–55° C. for thirty minutes.

Construct: Unless otherwise stated, the term "construct" refers to a recombinant genetic molecule comprising one or more isolated polynucleotide sequences of the invention.

Genetic constructs used for transgene expression in a host organism comprise (in the 5'-3' direction): a gene promoter sequence; an open reading frame coding for at least a functional portion of a polypeptide of the present invention; and a gene termination sequence. The open reading frame may be orientated in either a sense or anti-sense direction. The construct may also comprise selectable marker gene(s) and other regulatory elements for gene expression.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter controls the transcription or expression of the coding sequence. Generally, operably linked DNA sequences are contiguous and, where necessary, join two protein-coding regions in the same reading frame. With respect to polypeptides, two polypeptide sequences may be operably linked by covalent linkage, such as through peptide bonds or disulfide bonds.

Vector: The term "vector" refers to a nucleic acid molecule which is used to introduce a polynucleotide sequence into a host cell, thereby producing a transformed host cell. A "vector" may comprise genetic material in addition to the above-described genetic construct, e.g., one or more nucleic acid sequences that permit it to replicate in one or more host cells, such as origin(s) of replication, selectable marker genes and other genetic elements known in the art (e.g., sequences for integrating the genetic material into the genome of the host cell, and so on).

Transformed: A transformed cell is a cell into which has been introduced a nucleic acid molecule by molecular biology techniques. As used herein, the term transformation encompasses all techniques by which a nucleic acid molecule might be introduced into such a cell, plant or animal cell, including transfection with viral vectors, transformation by Agrobacterium, with plasmid vectors, and introduction of naked DNA by electroporation, lipofection, and particle gun acceleration and includes transient as well as stable transformants.

Isolated: An "isolated" biological component (such as a nucleic acid or protein or organelle) has been substantially separated or purified away from other biological components in the cell or the organism in which the component naturally occurs, i.e., other chromosomal and extra-chromosomal DNA and RNA, proteins and organelles. Nucleic acids and proteins that have been "isolated" include nucleic acids and proteins purified by standard purification methods. The term embraces nucleic acids including chemically synthesized nucleic acids and also embraces proteins prepared by recombinant expression in vitro or in a host cell and recombinant nucleic acids as defined below. As an example, a gene in a large genomic DNA fragment such as a contig is not sufficiently purified away from other biological components to be considered isolated due to the relatively large amount of extra DNA found in the average contig. As outlined below "recombinant nucleic acids" and "recombinant proteins" also are "isolated" as described above Recombinant: By "recombinant nucleic acid" herein is meant a nucleic acid that has a sequence that is not naturally occurring or has a sequence that is made by an artificial combination of two otherwise separated segments of sequence. This artificial combination is often accomplished by chemical synthesis or, more commonly, by the artificial manipulation of nucleic acids, e.g., by genetic engineering techniques, such as by the manipulation of at least one nucleic acid by a restriction enzyme, ligase, recombinase, and/or a polymerase. Once introduced into a host cell, a recombinant nucleic acid is replicated by the host cell; however, the recombinant nucleic acid once replicated in the cell remains a recombinant nucleic acid for purposes of this invention. By "recombinant protein" herein is meant a protein produced by a method employing a recombinant nucleic acid. As outlined above "recombinant nucleic acids" and "recombinant proteins" also are "isolated" as described above. A gene in a large fragment such as a contig would not be a "recombinant nucleic acid" given that artificial combination does not relate to the gene. However, if sequences around or within a gene in a contig have been manipulated for purposes relating to that gene (i.e., not merely because the gene is near the end of the contig), then such a gene in a contig would constitute a "recombinant nucleic acid" due to the relative proximity of the recombinant portion of the nucleic acid to the gene in question.

Complementary DNA (cDNA): A piece of DNA that is synthesized in the laboratory by reverse transcription of an RNA, preferably an RNA extracted from cells. cDNA produced from mRNA may include 5' and/or 3' noncoding sequences (i.e., 5' UTR, 3' UTR) but typically lacks internal, non-coding segments (introns) and regulatory sequences, such as promoters, that determine transcription.

Open reading frame (ORF): A continuous coding sequence of a gene flanked by a start and stop codon. An ORF lacks internal termination codons and can usually be translated into an amino acid sequence.

Non-naturally Occurring Plant: A non-naturally occurring plant is a plant that does not occur in nature without human intervention. Non-naturally occurring plants include transgenic plants and plants produced by non-transgenic means such as plant breeding.

Transgenic plant: As used herein, this term refers to a plant or tree that contains recombinant genetic material not normally found in plants or trees of this type and which has been introduced into the plant in question (or into progenitors of the plant) by human manipulation. Thus, a plant into which recombinant DNA is introduced by transformation is a transgenic plant, as are all offspring of that plant that contain the introduced transgene (whether produced sexually or asexually). It is understood that the term transgenic plant encompasses the entire plant or tree and parts of the plant or tree, for instance grains, seeds, flowers, leaves, roots, fruit, pollen, stems etc.

Standard molecular biology methods and plant transformation techniques can be used to produce transgenic plants that produce plants having a recombinant dmi1 gene.

Ortholog: Two nucleotide or amino acid sequences are orthologs of each other if they share a common ancestral sequence and diverged when a species carrying that ancestral sequence split into two species, sub-species, or cultivars. Orthologous sequences are also homologous sequences. Orthologous sequences hybridize to one another under high-stringency conditions. The term "polynucleotide", "oligonucleotide", or "nucleic acid" refers to a polymeric form of nucleotides of any length, either deoxyribonucleotides or ribonucleotides, or analogs thereof. The terms "polynucleotide" and "nucleotide" as used herein are used interchangeably. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A "fragment" or "segment" of a nucleic acid is a small piece of that nucleic acid.

Gene: A "gene" refers to a polynucleotide containing at least one open reading frame that is capable of encoding a particular protein after being transcribed and translated. In the present invention, the gene for DMI1 is described above.

Primer: The terms "primer" and "nucleic acid primer" are used interchangeably herein. A "primer" refers to a short polynucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a polymerase and at a suitable temperature and pH. The primer may be either single-stranded or double-stranded and must be sufficiently long to prime the synthesis of the desired extension product. The exact length of the primer will depend upon many factors, including temperature, source of primer and use of the method.

Polymerase chain reaction: A "polymerase chain reaction" ("PCR") is a reaction in which replicate copies are made of a target polynucleotide using a "primer pair" or a "set of primers" consisting of an "forward" and a "reverse" primer, and a catalyst of polymerization, such as a DNA polymerase, and particularly a thermally stable polymerase enzyme. Methods for PCR are taught in U.S. Pat. No. 4,683,195 (Mullis) and U.S. Pat. No. 4,683,202 (Mullis et al.). All processes of producing replicate copies of the same polynucleotide, such as PCR or gene cloning, are collectively referred to herein as "amplification" or "replication".

Mycorrhizal symbi sis: Mycorrhizal symbiosis is the association of a plant root with specific fungi. The fungus invades the root but the root does not develop a pathologic response. The plant host is believed to be secreting sugars and other organic materials to the fungus, while the fungus appears to convert minerals in the soil (such as phosphorus) and decaying organic material into forms accessible to the host.

Rhizobial symbiosis: Rhizobial symbiosis is the association of the root with specific nitrogen-fixing bacteria. Symbiosis with the bacterial species *Rhizobium* typically results in the formation of nodules on the roots of the plants; the *Rhizobium* live in these nodules. The bacteria receive energy in the form of carbon compounds from the plant, while the plants receive nitrogen in a usable form.

Nitrogen fixation: Nitrogen fixation is the conversion of gaseous nitrogen ($N_2$) to ammonia ($NH_3$) or nitrate ($NO_3^-$).

The present invention meets the needs for enhanced symbiosis in plants and methods and compositions for direct supplementation of soils with nitrogen and/or phosphorus. The initiation of the symbiosis between the leguminous plants and rhizobial bacteria is controlled by a molecular dialog between the two partners. Legume roots secrete specific exudates, essentially flavonoids, which induce the secretion by the bacteria of lipo-chitooligosaccharidic signals called Nod factors (Dénarié et al., 1996). Nod factors in turn, elicit plant responses that culminate in infection by rhizobia and the development of the root nodule. Extremely low concentrations ($10^{-9}$ to $10^{-12}$ M) of purified Nod factors trigger many of the same responses in the roots of legume hosts that are induced by symbiotic rhizobia. These responses include changes in ion fluxes, gene expression, and cell division (Long, 1996; Schultze and Kondorosi, 1998). Genetic screens in the model legume *Medicago truncatula* have identified mutants that are incapable of forming root nodules (Nod$^-$ phenotype). (Sagan et al., 1995; Cook et al, 1999; Penmetsa and Cook, 2000). Among these Nod$^-$ mutants, those impaired pleiotropically for early Nod factor responses were selected and separated into six complementation groups corresponding to the NFP, DMI1, DMI2, DMI3, NSP1 and NSP2 loci (Catoira et al., 2000; Ben Amor et al, 2003, Oldroyd and Long, 2003).

Phenotypic analyses have placed these genes into a hierarchy. NFP resides at the top of the cascade, as nfp mutants do not exhibit any of the known responses to Nod factor. DMI1 and DMI2 genes are necessary for the induction of calcium spiking in root hairs indicating that these genes must play a role upstream of DMI3, NSP1 and NSP2 (Wais et al., 2000), which are dispensable for this response.

Symbiosis with the bacterial species *Rhizobium* typically results in the formation of nodules on the roots of the plants. The *Rhizobia* live in these nodules and fix nitrogen. The bacteria receive energy in the form of organic compounds such as dicarboxyolic acids from the plant, while the plants receive nitrogen in a usable form, "fixed nitrogen." While not wishing to be bound by theory, it is thought that the nodule environment protects the nitrogenase enzyme from oxygen, which would impair the nitrogenase activity.

The dmi1, dmi2 and dmi3 mutants are also affected for the establishment of the mycorrhizal symbiosis (Nod⁻ Myc⁻ mutants) indicating that the signaling pathways of nodulation and mycorrhization share common components (Catoira et al., 2000; Geurts and Bisseling, 2002). In mycorrhizal symbiosis, specific fungi associate with the roots of a plant. The fungi invade the root but the root does not develop a pathologic response. The plant host is believed to be secreting sugars and other organic materials to the fungus, while the fungus appears to convert minerals (such as phosphorus) and other soil nutrients into forms accessible to the host. The molecular details of mycorrhizal symbiosis are not as well understood as those of rhizobial symbiosis.

Uses of the Invention

By way of example and not of limitation, the following uses of the invention are described and are therefore included in the scope of the invention:

The nucleic acid of the invention will be useful in identifying dmi1 and dmi1-related genes in other species. In addition, the dmi1 nucleic acid will be useful in designing probes that may be used to detect dmi1 and specific variants of dmi1. Such probes may be useful in breeding plants with particular dmi1 genes. Antisense nucleic acids and RNA inteference (RNAi) nucleic acids of the invention may be used to decrease the level of DMI1 transcripts in the cell, thereby decreasing the level of DMI1 protein in the cell, presumably altering the cell or organism's response to stimuli.

Transformation or transfection of prokaryotic or eukaryotic host cells with the nucleic acid of the dmi1 gene will be useful in amplifying, modifying, and characterizing the dmi1 gene and its encoded DMI1 protein. The primers and vectors of the invention will be useful for the same purposes. Modification of the dmi1 nucleic acid and the DMI1 amino acid sequence may entail mutagenesis, deletions, additions, fusions, or other alterations of various parts of the gene or protein in order to change its activity, thereby altering the effect of DMI1 on plant symbioses with mycorrhizae and rhizobia. Such mutations, deletions, substitutions, additions, and fusions of the dmi1 gene and protein are within the scope of the invention. dmi1 fusions may include the use of heterologous promoters to alter the regulation of the dmi1 gene.

It has been discovered that two nitrogen-fixing symbiants, *Mesorhizobium loti* and *Streptomyces* spp, contain relatively close homologs of dmi1. The nucleic acid of the dmi1 gene will be useful in determining what function if any dmi1 plays in these organisms.

The antibodies of the invention will be useful in identifying species with polypeptides having similar structural characteristics to the DMI1 polypeptide. Additionally the antibodies of the invention may be used to impair the activity of DMI1 in vitro or in vivo, thereby altering the cell or organism's response to stimuli. The DMI1 protein of the invention will be helpful in isolating other members of the pathways controlling plant mycorrhizal and rhizobial symbioses. For instance, the DMI1 protein may be used to identify ligands in the pathways.

The nucleic acid of the invention is useful in generating transgenic plants. The transgenic plants of the invention are useful in that such plants may exhibit improved levels of plant nutrition, as the plant will have increased levels of available phosphorus and/or nitrogen to utilize. Such transgenic plants may also improve the surrounding soil's nutrient quality, particularly with regards to levels of available nitrogen and phosphorus. Such transgenic plants may also be useful in decreasing the levels of nitrogen and phosphorus, where such levels are higher in a local environment than is desirable. Plants comprising mutations, deletions, substitutions, additions, and fusions of the dmi1 gene and protein may exhibit altered effects on plant symbioses with mycorrhizae and rhizobia. Such effect may result in altered plant nutrition, as the plant will have different levels of available phosphorus and/or nitrogen to utilize. Of particular interest is generation of important crop plants such as corn, wheat, barley, sorghum, oat, and rye that are capable of rhizobial symbiosis. Generating transgenic forms of such important crop plants expressing DMI1 as well as other genes in the symbiosis pathway may enable such important crop plants to form nodules with nitrogen fixing bacteria.

It is also of particular interest to increase the nitrogen-fixing capability of plants which already do so. Such plants include, but are not limited to soybean, common bean, pea, peanut, lentil, chickpea, cowpea, pigeon peas, alfalfa, and clover. In addition to the human and animal food produced by these plants, nitrogen-fixing legumes are also used as cover crops in which they are overseeded onto other crops such as wheat or oats, or grown in between crops to increase nitrogen content in the soil. Such cover or rotation crops include but are not limited to, crimson clover, hairy vetch, field peas, subterranean clover, red clover, white clover and sweetclover. There are also woody legumes such as Acacia and Albizia of which the leaves are consumed in a number of countries. Increasing the nitrogen fixation capability of these plants would also increase the usefulness of these nitrogen-fixing legumes as rotation or cover crops.

This invention will be better understood by reference to the following non-limiting embodiments.

Constructs

The present invention includes various aspects of nucleic acid sequences encoding DMI1 proteins. The simplest form of nucleic acid of the present invention is an isolated nucleic acid encoding a DMI1 protein or fragment thereof having some relevant DMI1 biological activity. Examples of such nucleic acids include nucleic acids that hybridize to the DMI1 nucleic acid disclosed herein under low, moderate, high or very high stringency, nucleic acids with 40%, 50%, 60%, 70%, 75%, 80%, 85%, 90%, 95%, or 97% identity to the DMI1 nucleic acids disclosed herein, and nucleic acids encoding a DMI protein with 40%, 50%, 60%, 70%, 75%, 80%, 85%, 90%, 95%, or 97% identity to the DMI1 proteins disclosed herein. In addition, the nucleic acids may include nucleic acids that encode proteins that share conserved regions with other DMI1 proteins when aligned with DMI1 protein families such as the *A. thaliana*, *O. sativa*, and *M. truncatula* proteins. Such conserved regions may share 70%, 75%, 80%, 85%, 90%, 95%, or 97% identity. Examples of conserved regions with 95% or greater identity in SEQ ID NO:12 include residues 345–376, 379–402, and 413–468.

In addition, the present invention includes the above nucleic acid sequences operably linked to a promoter. The preferred promoter is a heterologous promoter. The choice of promoter will be dictated by the target cell in which the DMI1 protein is to be expressed. Selection of an appropriate promoter functional in a desired target cell is routine in the art. One of skill in the art can use, for example, a constitutive promoter, an inducible promoter or a regulated promoter depending upon the desired pattern of expression. In addition to natural promoters, mutant promoters and artificial promoters created by splicing distinct regulatory elements may be used.

Another aspect of the present invention is vectors including the nucleic acids and promoter linked constructs described above. There are a wide range of vectors available to one of skill in the art. Such vectors can include, without limitation, expression vectors, cloning vectors, shuttle vectors, etc. which can include, but are not limited to, the following vectors or their derivatives: human, animal, or plant viruses such as vaccinia virus, adenovirus, cauliflower mosaic virus (CaMV), geminivirus, brome mosaic virus, and tobacco mosaic virus; insect viruses such as baculovirus; yeast vectors; bacteriophage vectors (e.g., lambda), and plasmid (e.g. the Ti plasmid of *Agrobacterium tumefaciens*) and cosmid DNA vectors, to name but a few. Selection of the appropriate vector will be dictated by the target cells, desired expression mode (e.g., transient expression versus permanent integration into the genome versus independently replicating vectors will cause one of skill in the art to select different vectors), and ease of recombinant manipulation. In some circumstances, one of skill in the art would use a shuttle vector that is functional in at least two organisms so that the nucleic acid may be manipulated in one organism and then transferred into the other.

Cells

The present invention encompasses cells containing the above constructs. The cells may be generated by standard molecular biology techniques discussed below. Preferred embodiments of the present invention include transgenic plants, plant cells, plant parts, and plant seeds. Preferred plants include, without limitation, monocots and dicots such as maize, sunflower, Brassica, cotton, sorghum, wheat, barley, millet, rice, cassava, potato, *Arabidopsis*, tomato, pepper, apple, spinach, or lettuce, legumes such as soybean, alfalfa, common bean, pea, peanut, lentil, chickpea, cowpea, pigeon peas, and clover. Other preferred embodiments include transgenic bacteria capable of fixing nitrogen.

Methods

The present invention also includes methods of making the constructs, vectors, transgenic cells and plants discussed above. The constructs and vectors may be generated using standard molecular biology techniques Introduction of the selected construct into plants is typically achieved using standard transformation techniques. The basic approach is to: (a) clone the construct into a transformation vector, which (b) is then introduced into plant cells by one of a number of techniques (e.g., electroporation, microparticle bombardment, *Agrobacterium* infection); (c) identify the transformed plant cells and regenerate whole plants from the identified plant cells, and (d) select progeny plants containing the introduced construct.

Preferably all or part of the transformation vector will stably integrate into the genome of the plant cell. That part of the transformation vector which integrates into the plant cell and which contains the introduced recombinant sequence may be referred to as the recombinant expression cassette.

Selection of progeny plants containing the introduced transgene may be made based upon the detection of the recombinant dmi1 gene in transgenic plants, upon the detection of the recombinant DMI1 or DMI1-related protein coding sequence or upon enhanced resistance to a chemical agent (such as an antibiotic) as a result of the inclusion of a selectable marker gene incorporated into the transformation vector.

Successful examples of the modification of plant characteristics by transformation with cloned nucleic acid sequences are replete in the technical and scientific literature. Selected examples, which serve to illustrate the knowledge in this field of technology include: U.S. Pat. No.5,571,706 ("Plant Virus Resistance Gene and Methods"); U.S. Pat. No.5,677,175 ("Plant Pathogen Induced Proteins"); U.S. Pat. No. 5,510,471 ("Chimeric Gene for the Transformation of Plants"); U.S. Pat. No. 5,750,386 ("Pathogen-Resistant Transgenic Plants"); U.S. Pat. No. 5,597,945 ("Plants Genetically Enhanced for Disease Resistance"); U.S. Pat. No. 5,589,615 ("Process for the Production of Transgenic Plants with Increased Nutritional Value Via the Expression of Modified 2S Storage Albumins"); U.S. Pat. No. 5,750,871 ("Transformation and Foreign Gene Expression in Brassica Species"); U.S. Pat. No. 5,268,526 ("Overexpression of Phytochrome in Transgenic Plants"); U.S. Pat. No. 5,780,708 ("Fertile Transgenic Corn Plants"); U.S. Pat. No. 5,538,880 ("Method for Preparing Fertile Transgenic Corn Plants"); U.S. Pat. No. 5,773,269 ("Fertile Transgenic Oat Plants"); U.S. Pat. No. 5,736,369 ("Method for Producing Transgenic Cereal Plants"); U.S. Pat. No. 5,610,049 ("Methods for Stable Transformation of Wheat"); U.S. Pat. No. 6,235,529 ("Compositions and Methods for Plant Transformation and Regeneration") all of which are hereby incorporated by reference in their entirety. These examples include descriptions of transformation vector selection, transformation techniques and the construction of constructs designed to express an introduced transgene.

The transgene-expressing constructs of the present invention may be usefully expressed in a wide range of higher plants where an altered mycorrhizal and/or rhizobial symbiosis response is useful.

Methods for the transformation and regeneration of monocotyledonous and dicotyledonous plant cells are known, and the appropriate transformation technique will be determined by the practitioner. The choice of method will vary with the type of plant to be transformed; those skilled in the art will recognize the suitability of particular methods for given plant types. Suitable methods may include, but are not limited to: electroporation of plant protoplasts; liposome-mediated transformation; polyethylene glycol (PEG-mediated transformation); transformation using viruses; micro-injection of plant cells; micro-projectile bombardment of plant cells; vacuum infiltration; and *Agrobacterium*-mediated transformation. Typical procedures for transforming and regenerating plants are described in the patent documents listed above.

Following transformation, transformants are preferably selected using a dominant selectable marker. Typically, such a marker will confer antibiotic or herbicide resistance on the seedlings of transformed plants, and selection of transformants can be accomplished by exposing the seedlings to appropriate concentrations of the antibiotic or herbicide. Suitable markers include, without limitation, those genes coding for resistance to the antibiotic spectinomycin or streptomycin (e.g., the aada gene), the streptomycin phosphotransferase (SPT) gene coding for streptomycin resistance, the neomycin phosphotransferase (NPTII) gene encoding kanamycin or geneticin resistance, the hygromycin phosphotransferase (HPT) gene coding for hygromycin resistance. After transformed plants are selected and grown the plant can be assayed for expression of recombinant proteins.

Proteins

The present invention further includes isolated DMI1 proteins and fragments thereof with DMI1 biological activity. The proteins may be isolated by routine techniques available to one of ordinary skill in the art. Such techniques include overexpression in desired target cells and purification therefrom. Standard methods of protein purification include chromatography (e.g., ion exchange, affinity, and sizing column chromatography), centrifugation, differential solubility, or by any other standard technique for the purification of proteins. Such standard techniques may be found in Robert K. Scopes, Protein Purification: Principles and Practice, Springer Verlag, 3$^{rd}$ Ed. 1996. In addition, affinity tags may be affixed to the protein via molecular biology to ease purification. Examples include his-tagging and flag-tagging the protein. The functional properties may be evaluated using any suitable assay Ligands The present invention includes ligands that interact with the above described proteins. Such ligands include small molecules, antibodies and other proteins. Antibodies may be generated by standard molecular biology techniques. Small molecule ligands may be identified by standard techniques available to one of ordinary skill in the art. With the automated screening techniques available today, large libraries may be screened with ease once pure protein is available. Such ligands may merely bind to the proteins while others may down regulate or completely inhibit the DMI1 biological activity or upregulate or activate the DMI1 biological activity.

Antibodies can be raised to a protein of the present invention, including individual, allelic, strain, or species variants, and fragments thereof, both in their naturally occurring (full-length) forms and in recombinant forms. Additionally, antibodies are raised to these proteins in either their native configurations or in non-native configurations. Anti-idiotypic antibodies can also be generated. Many methods of making antibodies are known to persons of skill.

In some instances, it is desirable to prepare monoclonal antibodies from various mammalian hosts, such as mice, rodents, primates, humans, etc. Description of techniques for preparing such monoclonal antibodies are found in, e.g., Basic and Clinical Immunology, 4th ed., Stites et al., Eds., Lange Medical Publications, Los Altos, Calif., and references cited therein; Harlow and Lane, Supra; Goding, Monoclonal Antibodies: Principles and Practice, 2nd ed., Academic Press, New York, N.Y. (1986); and Kohler and Milstein, Nature 256: 495–497 (1975).

Other suitable techniques involve selection of libraries of recombinant antibodies in phage or similar vectors (see, e.g., Huse et al., Science 246:1275–1281 (1989); and Ward, et al., Nature 341:544–546 (1989); and Vaughan et al., Nature Biotechnology, 14:309–314 (1996)). Alternatively, high avidity human monoclonal antibodies can be obtained from transgenic mice comprising fragments of the unrearranged human heavy and light chain Ig loci (i.e., minilocus transgenic mice). Fishwild et al., Nature Biotech., 14:845–851 (1996). Also, recombinant immunoglobulins may be produced. See, Cabilly, U.S. Pat. No. 4,816,567; and Queen et al., Proc. Nat'l Acad. Sci. 86:10029–10033 (1989).

The antibodies of this invention can be used for affinity chromatography in isolating proteins of the present invention, for screening expression libraries for particular expression products such as normal or abnormal protein, for raising anti-idiotypic antibodies which are useful for detecting or diagnosing various pathological conditions related to the presence of the respective antigens, for detecting expression of the DMI1 protein or allelic variants when breeding plants, and for down regulating or up regulating the activity of the DMI1 protein.

Kits

The present invention also includes kits useful for detecting the presence of the dmi1 nucleic acids and proteins of the present invention. Such kits may include molecules for the detection of the DMI1 genes and nucleic acids of the present invention such as nucleic acid probes for hybridization or primers for amplification and detection of DMI1. Alternatively, such kits may include molecules for the detection of the DMI1 proteins of the present invention such as the antibodies and ligands described above.

The present invention further includes kits useful in generating transgenic plants expressing the DMI1 protein. Such kits will include the constructs or vectors described above. In addition, the kits may contain additional materials useful for plant transformation as described above under methods.

EXAMPLE 1

Cloning DMI1 from *M. truncatula*

Figure 1:
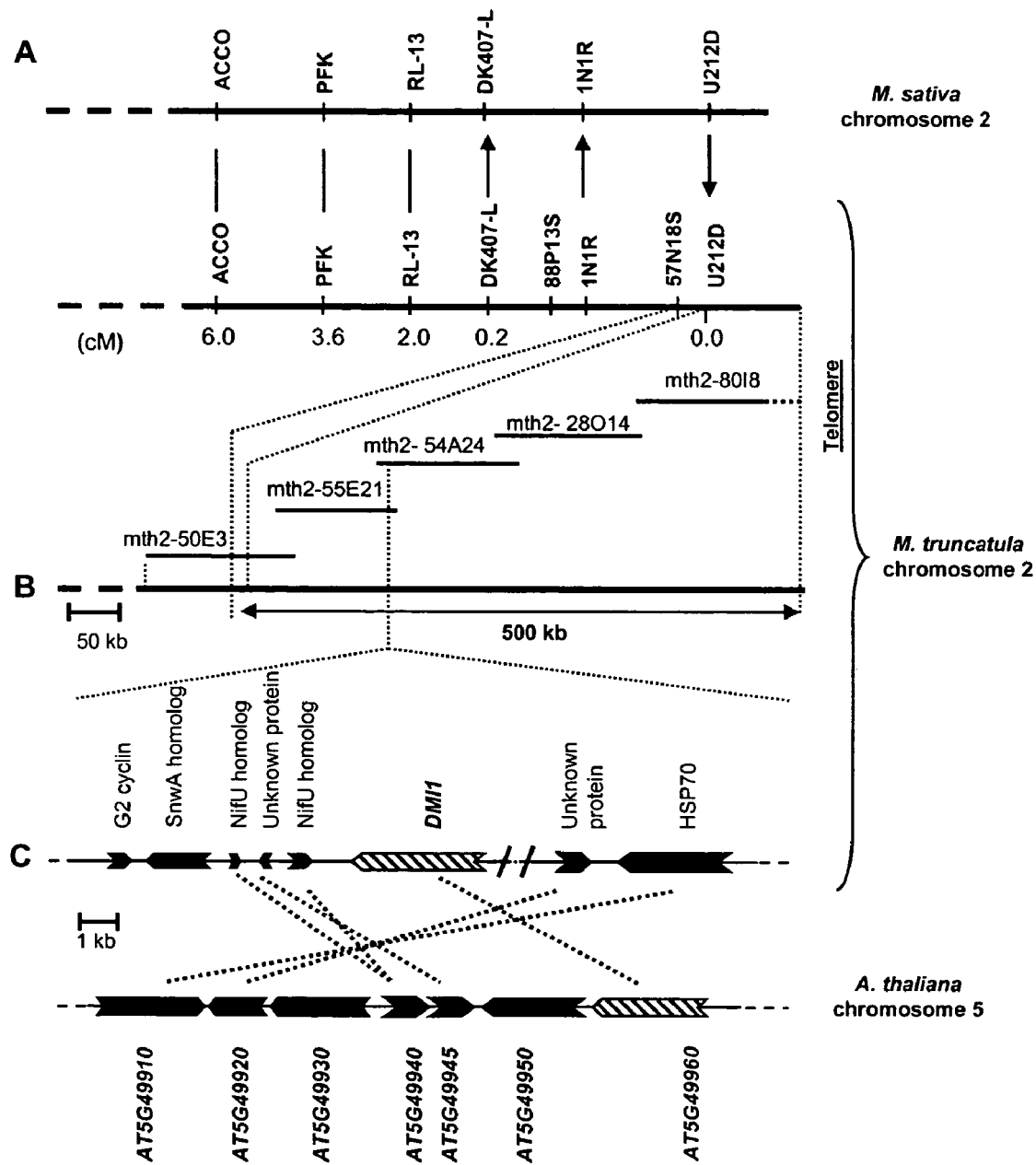
FIG. 1 shows the genetic and physical map of the DMI1 locus.

By means of genetic and cytogenetic analyses DMI1 was previously localized to one extremity of *M. truncatula* chromosome 2 (Ané et al. 2002). Genetic marker 1N1R, which defined the telomere end of linkage group 2 and was invariantly linked to the DMI1 locus in an F2 population of 499 Nod⁻ individuals, was used to seed a chromosome walk towards DMI1. In parallel to physical mapping, knowledge of chromosomal synteny between *M. truncatula* and *M. sativa* (Choi et al. 2003) was used to systematically position new genetic markers between 1N1R and the telomere. Genetic mapping of 1N1R in *M. sativa* revealed a single genetic marker, U212D, that was telomeric of 1N1R in both species (FIG. 1A). Using U212D as probe, additional BAC clones (e.g., mth2-50E3) of *M. truncatula* were identified and a 1.2 Mb contig extending from genetic marker 88P13S to the adjacent telomere of chromosome 2 was rapidly completed (FIG. 1).

Genotyping of >1,500 individuals identified a single recombination event that delimited DMI1 to a 550 kbp interval between genetic marker 57N18S and the telomere. The candidate gene approach was used to identify the gene. A minimum tiling path composed of 5 BAC clones (~550 kb in length) was sequenced using a BAC sublibrary shotgun strategy. Fgenesh (at the softberry.com/berry.phtml web site) predicted 85 genes in the sequenced region, roughly half of which were supported by unigene assignments in the *M. truncatula* EST data. Oligonucleotide primers were designed for candidate genes and the polymerase chain reaction was used to amplify both genomic DNA and cDNA isolated from independent DMI1 alleles, including 3 ethylmethane sulfonate (EMS) and 2 fast neutron bombardment (FNB) mutants. A single unknown protein gene on BAC mth2-54A24 was altered in each of five independent alleles (Table 1) with strong affects on the transcript and/or predicted protein structure. To confirm the identity of this gene as DMI1, we verified the ability of a wild type DMI1 transgene to complement the Nod⁻ phenotype of DMI1 alleles C71 and Y6 (FIG. 2).

A full-length DMI1 cDNA was cloned from *M. truncatula* root mRNA and determined to encode a 2,649 bp open reading frame with a deduced protein of 883 amino acids. Predicted features of the protein include 4 trans-membrane domains, the first two of which encompass a putative leucine zipper (LZ) motif, and a proline rich domain that could facilitate protein-protein interactions (Bornberg-Bauer et al. 1998). Other than these general features, the DMI1 protein lacks even moderate similarity to functionally characterized proteins or protein sub-domains in plants, although as described below the protein is well conserved throughout most lineages of land plants that have been sampled by EST and genome sequencing projects.

EXAMPLE 2

Transgenic Complementation of DMI1 in Plant Root

To confirm that the identified gene was DMI1, we analyzed the ability of wild type DMI1 gene to complement the Nod⁻ Myc⁻ phenotype of the mutants. In a previous study, we have shown that the nodulation phenotype of the dmi mutants is determined by the genotype of the root (Ané et al., 2002). As such it was possible to use the *Agrobacterium rhizogenes* mediated transformation to complement the dmi1 mutation (Boisson-Dernier et al., 2001).

The full length wild type DMI1 cDNA was amplified in a pCR2.1 vector (Invitrogen). 1.6 kb of the promoter sequence was also amplified from mth2-54A24 and cloned upstream of the cDNA. The whole construct was introduced into the pCAMBIA-1303 binary vector (clone pCAMBIA-DMI1). *A. rhizogenes* strain Arqua1 containing the pCH32 vector carrying virE and virG virulence genes was used for transformation. pCAMBIA-DMI1 and pCAMBIA-1303 (as a negative control) were introduced into Arqua1 (pCH32) strain. Roots of DMI1 and wild type plants were transformed with either the DMI1 cDNA under control of the native promoter or with vector alone. Transformed roots were inoculated with *Sinorhizobium meliloti* and nodule development was scored visually after 15 days. A constitutively expressed uidA gene was used as a reporter to identify transformed tissues based on GUS staining. Among more than 80 independent DMI1 transformants, only those transformed by the DMI1 transgene were nodulated by *S. meliloti*, while transformation of wild type plants with either DMI1 or control constructs had no effect on nodulation. The restoration of the Nod⁺ phenotype clearly confirmed that we had cloned DMI1 (FIG. 2).

EXAMPLE 3

Expression Analysis of DMI1

The expression of DMI1 was analyzed by means of semi-quantitative RT-PCR (FIG. 3A). RNAs were extracted using RNeasy Plant Minikit (Qiagen, Germany) and quantified with Ribogreen RNA quantitation kit (Molecular Probes, USA). RT-PCR experiments were performed using the PowerScript™ RT-PCR kit (Clontech laboratories, USA). The results indicated that DMI1 is constitutively expressed in roots, with lower levels of transcript detected in pods, flowers, leaves and stems. Treatments known to activate expression of plant "nodulin genes", including inoculation with the compatible symbiotic bacterium *Sinorhizobium meliloti* (FIG. 3B) or $10^{-9}$ M cognate Nod factors (data not shown), had no effect on DMI1 transcript levels.

EXAMPLE 4

Analysis of the Gene Structure and Homologs

A growing body of evidence indicates that the signalling pathway leading to nodulation is highly conserved across legume species and that diverse legume species are likely to contain orthologous signalling components (Endre et al. 2002). Southern blot experiments indicate that DMI1 is a single copy gene in *M. truncatula*, with homologs present in many other leguminous plants, including *Medicago sativa*, *Melilotus alba*, *Vicia hirsuta*, *Lotus japonicus*, *Sesbania*, *Cassia*, *Trifolium*, *Desmodium*, *Vigna*, *Macroptilium* and *Vigna radiata* (data not shown). BLASTN analyses identified highly similar ESTs in soybean and *L. japonicus* indicating that the sequence homologs in these species represent expressed genes.

Figure 4A:
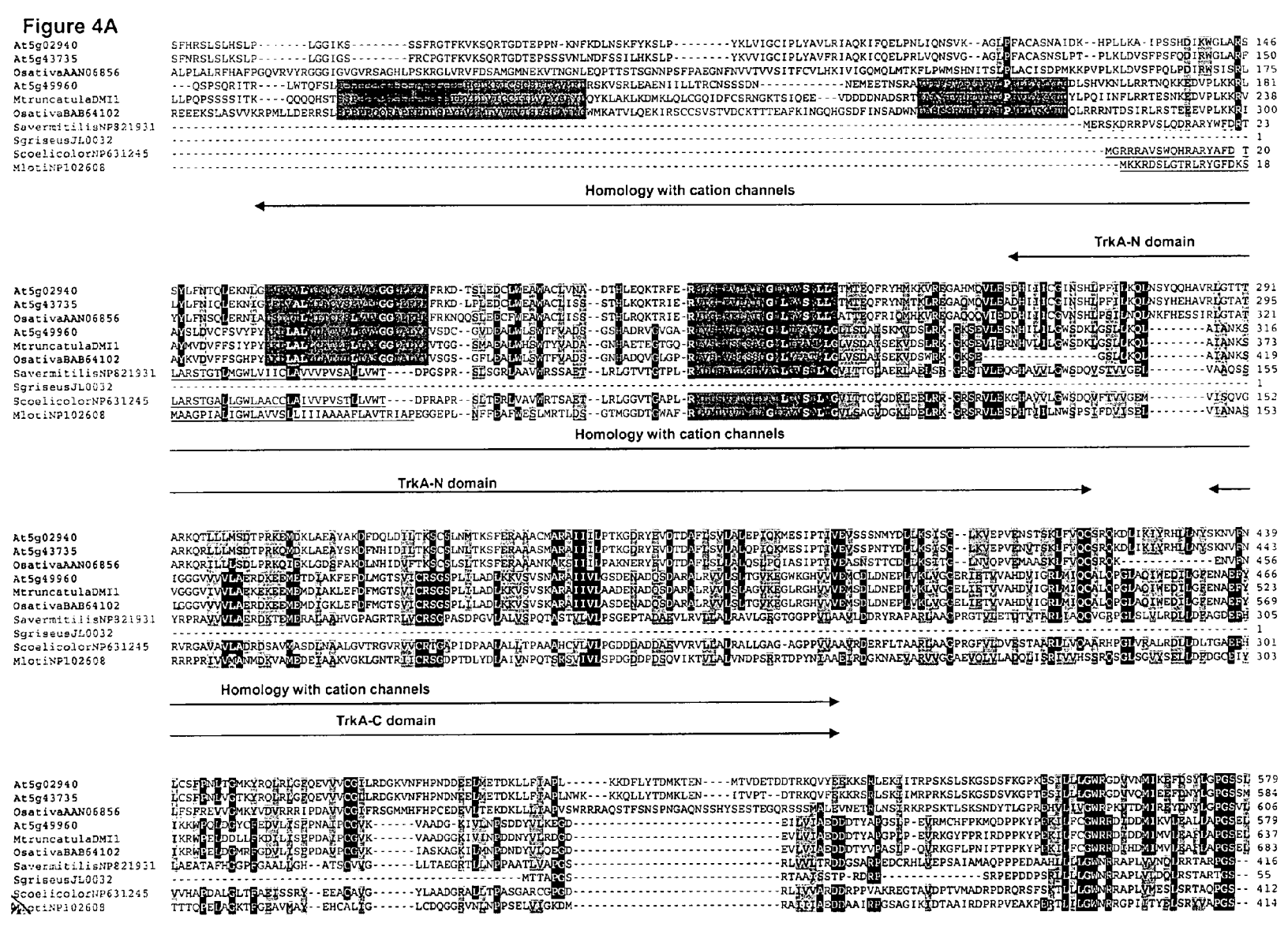
Figure 4B:
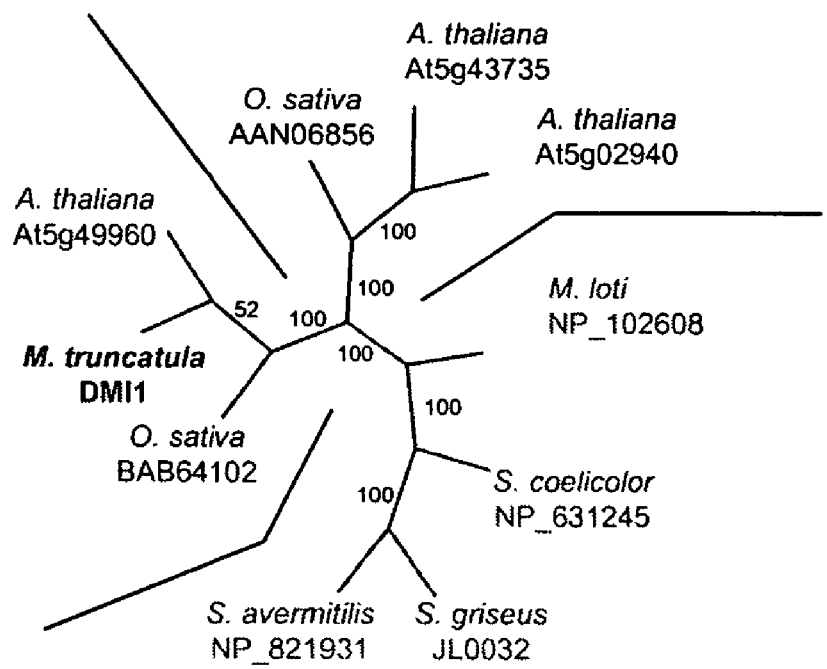

BLASTX and TBLASTN searches of the NCBI non-redundant and EST databases revealed with highly similar proteins predicted in over 28 monocot and dicot species, and a more distant homolog in the non-vascular plant *Physcomitrella patens*. Related sequences were not identified in the fully sequenced genomes of other eukaryotes, including animals, fungi, or green algae. Instead, relatively close homologs were identified in two eubacterial genera, namely the nitrogen fixing symbiont *Mesorhizobium loti* and *Streptomyces* spp. Surprisingly, homologous genes were not evident in any other sequenced bacterial genome, including close relatives of *M. loti* such as *Sinorhizobium meliloti* and *Agrobacterium tumefaciens*. Phylogenetic reconstruction based on parsimony analysis was used to infer the evolutionary history of this gene family. Analysis of several full-length deduced proteins from *M. truncatula*, *Arabidopsis*, rice and bacterial species yielded three well supported clades, corresponding to two paralogous groups of plant genes and a single group of bacterial genes (FIG. 4B).

The complete sequence of DMI1 putative orthologous genes was available for the *A. thaliana* At5g49960 and rice BAB64102 genes, corresponding to single copy genes on chromosomes 5 and 1 respectively. The *Arabidopsis* and *M. truncatula* loci, but not their rice counterpart, reside in a region of conserved genome microsynteny, presumably indicative of the ancestral chromosomal context (FIG. 1C). The *A. thaliana* and rice predicted proteins share 80% identity with DMI1, with the highest similarity found in the C-terminal region. Although ESTs corresponding to the *A. thaliana* gene were absent from the public databases semi-quantitative RT-PCR analysis indicates that the Arabidopsis gene is expressed in roots but not in leaves (FIG. 3A).

Comparison of the deduced partial protein *Physcomitrella patens* with either group of angiosperm paralogs indicates that all three groups are roughly equally diverged from one another (i.e., 26–28% identity and 53–56% similarity), consistent with an origin in the non-vascular plants. Taken together with the absence of homologs in the fungal, animal and algal lineages, these results suggest that the DMI1 protein represents a plant-specific innovation that potentially arose near the base of the land plant lineage. Interestingly, the fact that the *M. loti* and *Streptomyces* sequences also branch from the base of the DMI1 lineage, near the inferred plant duplication, is suggestive of horizontal transfer from an ancient plant genome(s) to a limited number of bacterial species.

DMI1 is predicted to act in genetic proximity to two additional *M. truncatula* genes, DMI2 and DMI3, which together comprise the set of known genes common to both mycorrhizal and rhizobial symbioses (Catoira et al. 2000). All three DMI genes are implicated in transduction of the Nod factor signal; DMI1 and DMI2 are required for Nod factor-induced calcium spiking, which by analogy to animal systems is predicted to have a causal role in the Nod factor signal transduction cascade. Despite the fact that DMI1 homologs have been identified in the bulk sequencing projects of many plant species, DMI1 represents the first member of this gene family with an assigned phenotype and verified gene structure. As with the previously identified NORK receptor kinase (DMI2) (Endre et al. 2002), DMI1 is predicted to be a membrane spanning protein and may participate in the formation of a receptor-complex for symbiotic signals. The fact that proline-rich and leucine zipper domains often participate in protein-protein interactions supports the idea of such a protein complex, but these motifs are present in the N-terminus of DMI1, a region of the protein that is poorly conserved among the various homologs. Together, the homologs of *Arabidopsis*, rice, *Mesorhizobium* and *Streptomyces* proteins comprise the DUF1012 protein family in the Pfam database (at the sanger.ac.uk/Software/Pfam/web site), without functional assignment. Pfam identifies the so-called DUF1012 domain as a defining feature of this protein family, which in the case of DMI1 overlaps substantially with a domain of low, but broad similarity to the NAD-binding TrkA domain of certain bacterial potassium channels (Anantharaman et al. 2001). The central portion of DMI1, commencing at the third predicted transmembrane domain through the entire TrkA homology region, is predicted to share distant homology with the well-characterised potassium channels of certain archaea (FIG. 4A). More generally, proteins of this family are implicated as cation channels in both prokaryotes and eukaryotes. The crystal structure of the *Methanobacterium thermoautotrophicum* protein MthK reveals a multimeric $K^+$ channel that is ligand-gated by $Ca^{2+}$ (Jiang et al. 2002). DMI1 is conserved throughout both the pore and ring domains that are thought to constitute the functional cation channel (Jiang et al. 2002), but degenerate in the filter region, located between transmembrane domains 3 and 4, where structural modifications have been correlated with altered cation specificity (Maser et al. 2002). Whether DMI1 and its close phylogenetic relatives in plants and bacteria might also function as ligand-gated cation channels remains uncertain, but the possibility is particularly intriguing given the genetic requirement for DMI1 function in Nod factor induced calcium oscillations within *Medicago* root hair cells.

If DMI1 is membrane-localised, it will be important to resolve the cellular localisation (intracellular or extracellular) of the DMI1 N— and C-termini. An extracellular ligand-binding domain could facilitate perception of symbiotic signals, while an intracellular location might suggest a role in downstream signal transduction events. Similarly, identifying DMI1-interacting proteins should also expand our understanding of the role of the DMI1 protein in symbiotic interactions. Candidate proteins to interact with DMI1 include LYK3 and 4/NFR1 and 5 (Limpens et al. 2003, Radutoiu et al 2003, Madsen et al. 2003, Parniske et al. 2003), NFP (Amor et al. 2003), DMI2 (Endre et al. 2002, Stracke et al. 2002), and DMI3 (Catoira et al. 2000), in addition to other proteins not yet identified in molecular or genetic screens.

Approximately 80% of terrestrial plants establish mycorrhizal symbioses. These beneficial plant-fungal associations act to expand the effective root-soil interface; in addition to their importance in natural and agricultural ecosystems, they may have facilitated the colonization of land by plants by increasing access to vital soil nutrients in the primitive root-like structures of non-vascular plants (Heckman et al. 2001). The high degree of conservation for DMI1 orthologs among angiosperms (>80% similarity among rice, *Arabidopsis* and *Medicago* proteins) and the fact that only a single gene with high similarity to DMI1 is present in the fully sequenced genomes of rice and *Arabidopsis*, suggests that the biological and molecular function of this group of proteins is also likely to be conserved. By comparison, other genes that have been recently identified for Nod factor signalling (i.e., LYK homologs, DMI2) are less well conserved among angiosperms, and in the case of LYK homologs and DMI2 appear to be members of large, fast evolving gene families. It is widely anticipated that nodulation in legumes arose from an ancient, conserved pathway for mycorrhizal associations, and we suggest that DMI1 is a pivotal component of this pathway.

REFERENCES AND NOTES

The following references and notes are hereby incorporated by reference in their entirety:

1. B. B. Amor et al., *Plant J.* 34, 495–506. (2003).
2. V. Anantharaman, E. V. Koonin, L. Aravind, *J Mol Biol* 307, 1271 (2001).
3. J. M. Ané et al., *Mol. Plant Microbe Interact.* 15, 1108–18. (2002).
4. A. Boisson-Dernier et al., *Mol. Plant Microbe Interact.* 14, 695–700 (2001).
5. E. Bornberg-Bauer, E. Rivals, M. Vingron, *Nucleic Acids Res.* 26, 2740–6. (1998).
6. R. Catoira et al., *Plant Cell* 12, 1647–1666 (2000).
7. H. K. Choi et al., *Genetics in press* (2003).
8. D. R. Cook, *Curr. Opin. Cell Biol.* 2, 301–304 (1999).
9. J. V. Cullimore, R. Ranjeva, J. J. Bono, *Trends Plant Sci.* 6, 24–30 (2001).
10. M. den Hartog, A. Musgrave, T. Munnik, *Plant J.* 25, 55–65 (2001).
11. J. Dénarié, F. Debellé, J. C. Promé, *Annu. Rev. Biochem.* 65, 503–535 (1996).
12. G. Endre et al., *Nature* 417, 962–966 (2002).
13. M. E. Etzler et al., *Proc. Natl. Acad. Sci. USA* 96, 5856–5861 (1999).
14. R. Geurts, T. Bisseling, *Plant Cell* 14, 239–249 (2002).
15. F. Gressent et al., *Proc. Natl. Acad. Sci. USA* 96, 4704–4709 (1999).
16. D. S. Heckman et al., *Science* 293: 1129 (2001).
17. Y. Jiang et al., *Nature* 417, 515 (2002).
18. E. Limpens et al., *Science* 28, 28 (2003).
19. S. R. Long, *Plant Cell* 8, 1885–1898 (1996).
20. E. B. Madsen et al., *Nature* 425: 637 (2003).
21. P. Maser et al., *PNAS* 99, 6428 (2002).
22. T. D. McKnight, K. Riha, D. E. Shippen, *Plant Mol. Biol.* 48, 331–7. (2002).
23. Y. W. Nam et al., *Theor. Appl. Genet.* 98, 638–646 (1999).
24. H. Nielsen, J. Engelbrecht, S. Brunak, G. von Heijne, *Protein Eng.* 10, 1–6. (1997).
25. K. Novak, *J. Hered.* 94, 191–3. (2003).
26. G. E. Oldroyd, S. R. Long, *Plant Physiol.* 131, 1027–32. (2003).
27. M. Parniske and J. A. Downie, *Nature* 425, 569 (2003).
28. R. V. Penmetsa, D. R. Cook, *Plant Physiol.* 123, 1387–1398 (2000).
29. J. L. Pingret, E. P. Journet, G. D. Barker, *Plant Cell* 10, 659–671 (1998).
30. S. Radutoiu, et al., *Nature* 425:585 (2003).
31. M. Sagan, D. Morandi, E. Tarenghi, G. Duc, *Plant Sci.* 111, 63–71 (1995).
32. M. Schultze, A. Kondorosi, *Annu. Rev. Genet.* 32, 33–57 (1998).
33. S. Stracke et al., *Nature* 417, 959–962 (2002).
34. P. Thoquet et al., *BMC Plant Biol.* 2, 1 (2002).
35. R. J. Wais et al., *Proc. Natl. Acad. Sci. USA* 97, 13407–13412 (2000).

TABLE 1

Summary of *M. truncatula* dmi1 alleles

| Mutagenesis | DMI1 mutant | Nature of mutations |
|---|---|---|
| EMS | B129 | G1068A point mutation that results in a premature stop codon truncating the protein at amino acid position 356 |
| EMS | C71 (domi) | G1264A point mutation that occurs at the 5' splice site of the third intron and that causes a mis-splicing event |
| EMS | Y6 | C913T point mutation that creates a premature stop codon truncating the protein at amino acid position 305 |
| FNB | GY15-3F-4 | Large deletion of all the 5' of the gene and the promoter |
| FNB | GY15-1B-5.1 | Large deletion of all the 5' of the gene and the promoter |

We claim:

1. An isolated nucleic acid comprising SEQ ID NO: 11 or the complement thereof.

2. An isolated nucleic acid encoding a polypeptide having at least 95% sequence identity to SEQ ID NO:12, wherein the polypeptide confers increased root nodulation.

3. An isolated nucleic acid encoding a polypeptide comprising SEQ ID NO:12.

4. A recombinant nucleic acid comprising the nucleic acid of claim 3, wherein said recombinant nucleic acid is operably linked to a promoter sequence.

5. A prokaryotic or eukaryotic host cell comprising the nucleic acid of claim 3.

6. A vector comprising the nucleic acid of claim 3.

7. A prokaryotic or eukaryotic host cell comprising the vector of claim 6.

8. A transgenic plant comprising an exogenous nucleic acid selected from the group consisting of:
   a) an exogenous nucleic acid comprising SEQ ID NO:11,
   b) an exogenous nucleic acid comprising the complement of SEQ ID NO:11,
   c) an exogenous nucleic acid encoding a protein comprising SEQ ID NO:12, and
   d) an exogenous nucleic acid encoding a polypeptide having at least 95% sequence identity to SEQ ID NO:12, wherein the polypeptide confers increased root nodulation.

9. A transgenic seed produced from the transgenic plant of claim 8.

10. A method of increasing root nodulation in a plant comprising introducing into the plant an exogenous nucleic acid selected from the group consisting of:
   a) an exogenous nucleic acid comprising SEQ ID NO:11,
   b) an exogenous nucleic acid comprising the complement of SEQ ID NO:11, encoding a protein comprising SEQ ID NO:12, and
   c) an exogenous nucleic acid encoding a protein comprising SEQ ID NO:12, and
   d) an exogenous nucleic acid encoding a polypeptide having at least 95% sequence identity to SEQ ID NO:12, wherein the polypeptide confers an increased root nodulation.

11. A transformed cell or plant with an increased accumulation of nitrogen or phosphorus, wherein said increased accumulation is relative to a similar cell or plant, wherein the cell or plant with said increased accumulation of nitrogen or phosphorus differs in comprising an exogenous nucleic acid selected from the group consisting of:
   a) an exogenous nucleic acid comprising SEQ ID NO:11,
   b) an exogenous nucleic acid comprising the complement of SEQ ID NO:11,
   c) an exogenous nucleic acid encoding a protein comprising SEQ ID NO:12, and
   d) an exogenous nucleic acid encoding a polypeptide having at least 95% sequence identity to SEQ ID NO:12, wherein the polypeptide confers an increased root nodulation.

12. An isolated nucleic acid selected from the group consisting of:
   a) the nucleic acid comprising SEQ ID NO:13,
   b) a nucleic acid comprising the complement of SEQ ID NO:13,
   c) a nucleic acid encoding the protein comprising SEQ ID NO:14, and
   d) a nucleic acid encoding a polypeptide having at least 95% sequence identity to SEQ ID NO:14, wherein the polypeptide confers increased root nodulation.

13. The nucleic acid of claim 12, wherein the nucleic acid encodes SEQ ID NO:14.

14. The transgenic plant of claim 8 wherein the exogenous nucleic acid comprises SEQ ID NO:11.

15. The transgenic plant of claim 8 wherein the exogenous nucleic acid encodes a protein comprising SEQ ID NO:12.

16. Transgenic seed from tho plant of claim 14.

17. Transgenic seed from the plant of claim 15.

* * * * *